(12) United States Patent
Kimura

(10) Patent No.: US 7,627,360 B2
(45) Date of Patent: Dec. 1, 2009

(54) MRI APPARATUS, FLOW QUANTIFICATION APPARATUS, AND FLOW QUANTIFICATION METHOD FOR ASL IMAGING

(75) Inventor: Tokunori Kimura, Yaita (JP)

(73) Assignee: Kabushiki Kaisha Toshiba, Minato-Ku, Tokyo (JP)

( * ) Notice: Subject to any disclaimer, the term of this patent is extended or adjusted under 35 U.S.C. 154(b) by 932 days.

(21) Appl. No.: 10/435,682

(22) Filed: May 12, 2003

(65) Prior Publication Data

US 2004/0030240 A1 Feb. 12, 2004

(30) Foreign Application Priority Data

May 13, 2002 (JP) ............................. 2002-137697

(51) Int. Cl.
*A61B 5/05* (2006.01)
(52) U.S. Cl. ...................... 600/419; 600/407; 600/410; 324/306; 324/307; 324/309
(58) Field of Classification Search ................ 600/410, 600/419; 324/306, 307, 309
See application file for complete search history.

(56) References Cited

U.S. PATENT DOCUMENTS

| 5,846,197 | A | * | 12/1998 | Edelman | ...................... 600/419 |
| 6,717,405 | B2 | * | 4/2004 | Alsop | .......................... 324/306 |
| 6,980,845 | B1 | * | 12/2005 | Alsop | .......................... 600/410 |
| 2003/0211036 | A1 | * | 11/2003 | Degani et al. | .............. 424/1.11 |

OTHER PUBLICATIONS

Kimura, Tokunori. "Non-Invasive Perfusion Imaging by Modified STAR Using Asymmetric Inversion Slabs (ASTAR)." 2000. Japanese Journal of Magnetic Resonance in Medicine. vol. 20, No. 8.pp. 374-385. (Abstract provided).*

Wong et al, "Velocity Selective Arterial Spin Labeling", Proc. Intl. Soc. Mag. Reson. Med. 10 (2002).

Norris et al, "Velocity Selective Radiofrequency Pulse Trains", Journal of Magnetic Resonance 137, 231-236 (1999).

Edelman et al, "Qualitative Mapping of Cerebral Blood Flow and Functional Localization with Echo-Planar MR Imaging and Signal Targeting with Alternating Radio Frequency", Radiology 1994; 192:513-520.

Haase, :Snapshot Flash MRI, Applications to T1, T2, and Chemical-Shift Imaging, Magnetic Resonance in Medicine 13, 77-89 (1990).

Dwong et al, "MR Perfusion Studies with T1-Weighted Echo Planar Imaging", MRM 34:878-887 (1995).

Mai et al, "Alternative of Selective Inversion Pulses (ASI): An MR Perfusion Imaging Technique with Shorter Transit Time of Labeled Blood Than Signal Targeting Alternating Radiofrequency (STAR)", ISMRM 1998.

(Continued)

*Primary Examiner*—Brian Casler
*Assistant Examiner*—James Kish
(74) *Attorney, Agent, or Firm*—Nixon & Vanderhye PC

(57) ABSTRACT

An MRI apparatus is provided to quantify perfusion (microcirculatory blood flow in the tissue) in a region to be imaged in a subject based an ASL (arterial spin labeling) technique. The apparatus comprises imaging, storing, and flow quantifying units. The imaging unit performs a scan according to the ASL technique on the region so that image data is acquired from the region. The storing unit stores relationship information between a concentration of tracer (water) and a flow of the perfusion. The relationship is obtained on a two-compartment model that uses two compartments placed inside and outside of a flow of blood that diffuses into the tissue of the region and that considers temporal changes in the diffusion of the microcirculatory blood flow into the tissue. The flow quantifying unit quantifies the flow of the perfusion by applying an amount derived from the image data to the relationship information.

8 Claims, 21 Drawing Sheets

OTHER PUBLICATIONS

Edelman et al, "Epistar MRI: Multislice Mapping of Cerebral Blood Flow", MRM 40:800-805 (1998).

Silva et al, "Multi-Slice MRI of Rat Brain Perfusion During Amphetamine Stimulation Using Arterial Spin Labeling", MRM 33:209-214 (1995).

Alsop et al, "Multisection Cerebral Blood Flow MR Imaging with Continuous Arterial Spin Labeling", Radiology 1998: 208:410-416.

Mani et al, :"Background Suppression with Multiple Inversion Recovery Nulling: Applications to Projective Angiography", MRM 37:898-905 (1997).

* cited by examiner (a) PASL:
$Ca(t) = A_* Mo_{i*} \exp[-t/T1i]$ : $\tau d < t < Ttag + \tau d$ (b) CASL:
$Ca(t) = A_* Mo_{i*} \exp[-\tau d/T1i]$ : $\tau d < t < Ttag + \tau d$ Ttag : tag duration time
$\tau d$ : transit delay time

TABLE 1

| method tissue | two compartment model (theoretical) | single compartment model | Linear Scaling (CBF=K*Qt) |
|---|---|---|---|
| W M | 20 (1) | 28.7 (1.435) | 21.3 (1.067) |
| G M | 80 (1) | 74.8 (0.935) | 79.7 (0.996) |

FIG. 9A

TABLE 2

| tissue | Frontal W.M. | Parietal W.M. | Frontal Cortex | Parietal Cortex | Thalamus | Hemisphere |
|---|---|---|---|---|---|---|
| Xe-CT CBF | 18.7±5.1 | 19.1±4.8 | 39.7±9.0 | 36.4±8.7 | 58.4±12.2 | 38.5±4.8 |
| ASL CBF | 21.3±5.9 | 26.7±4.3 | 36.8±10.9 | 42.7±9.3 | 56.9±9.5 | 43.0±7.8 |

FIG. 9B

| # | model | method tissue T1(T1e) | PASL CBF G M | PASL CBF W M | CASL CBF G M | CASL CBF W M |
|---|---|---|---|---|---|---|
| 1 | two compartment (PS=130[ml/100cc/min]) | tissue(0.9s:GM, 0.7s:WM) | 80.0(1.00) | 20.0(1.00) | 80.0(1.00) | 20.0(1.00) |
| 2 | | mean(0.8s) | 82.4(1.03) | 19.5(0.97) | 84.6(1.06) | 19.1(0.96) |
| 3 | | blood(1.2s) | 75.0(0.94) | 18.1(0.90) | 69.4(0.87) | 16.2(0.81) |
| 4 | single compartment (PS=∞) | tissue(0.9s:GM, 0.7s:WM) | 74.8(0.94) | 25.1(1.26) | 73.6(0.92) | 25.7(1.29) |
| 5 | | mean(0.8s) | 80.9(1.01) | 22.5(1.13) | 82.4(1.03) | 22.4(1.12) |
| 6 | | blood(1.2s) | 62.3(0.78) | 17.2(0.86) | 56.23(0.70) | 15.3(0.77) |
| 7 | Linear scaling : f=K [deltaM/Moi] | | 79.4(0.99) | 22.3(1.11) | 79.5(0.99) | 21.9(1.09) |

| | | |
|---|---|---|
| K ( when A=1 ) | 17854 | 7260 |
| K ( when A=2 ) | 8927 | 3630 |

FIG. 12

FLOW CALCULATION BASED ON LINEAR SCALING
(FLOW CALCULATION USING FUNCTION OR TABLE DEFINING Qt vs. f)

FLOW CALCULATION BASED ON POLYNOMIAL APPROXIMATION
(FLOW CALCULATION USING FUNCTION OR TABLE DEFINING Qt vs. f)

| Qt | | Qt1 | Qt2 | Qt3 | ——— Qtn |
|---|---|---|---|---|---|
| F[ml/100cc/min] | | F1 | F2 | F3 | ·········· Fn |

FUNCTION OF Qt vs. f FOR EACH TI
( POLYNOMIAL APPROXIMATION )

Relationship between Control-IR
and Tag-IR slabs in ASTAR (PASL)

FLOW CALCULATION BASED ON LINEAR SCALING
(FLOW CALCULATION USING FUNCTION OR TABLE DEFINING Qt vs. f)

FLOW CALCULATION BASED ON POLYNOMIAL APPROXIMATION
(FLOW CALCULATION USING FUNCTION OR TABLE DEFINING Qt vs. f)

MRI APPARATUS, FLOW QUANTIFICATION APPARATUS, AND FLOW QUANTIFICATION METHOD FOR ASL IMAGING

BACKGROUND OF THE INVENTION

1. Field of the Invention

The present invention relates to an MRI (magnetic resonance imaging) apparatus and a flow quantification method with regard to ASL (arterial spin labeling) imaging, which can quantify flow with a simple method using imaging based upon the ASL method which can provide images of perfusion or blood vessels, without administrating a contrast medium. It is noted that the ASL method described in the present invention indicates all the spin labeling methods in the broad sense.

2. Description of the Related Art

Magnetic resonance imaging is a method wherein nuclear spins of a subject in a static magnetic field are magnetically excited by radio frequency (RF) signals with a Larmor frequency so as to obtain an image from FID (self induced decay) signals or echo signals, accompanying the excitation.

As one category of magnetic resonance imaging, the spin labeling method, i.e., the ASL method for evaluating perfusion for tissue has been known. The ASL method is a method for providing perfusion images and the like, reflecting the blood vessel image or micro circulation of a subject, without administering a contrast medium, i.e., in a noninvasive manner, and in recent years, research has been actively made with regard to the ASL method. In particular, clinical applications have been made mainly with regard to cerebral blood flow (CBF) of the head, and furthermore, quantification of blood flow is becoming possible.

The ASL method is roughly classified into the continuous ASL (CASL) method and the pulsed ASL (PASL) method (also referred to as dynamic ASL (DASL)). The CASL method is a method wherein great, continuous, and adiabatic RF is applied, the spin state within blood vessels is labeled (magnetized) at a certain point in time, and the change in signals following the labeled-blood bolus reaching an imaging slab (observation face) is imaged. On the other hand, the PASL method is a method wherein pulse-shaped adiabatic RF, the magnetization in blood vessels is changed at all times, and imaging is performed for the tissue having magnetized blood flow continuously, thereby evaluating the perfusion of the tissue. The PASL method can be relatively easily performed with a clinical-use MRI apparatus.

With the ASL imaging, in general, two images of the control mode and the label (tag) mode are generated. The image data sets obtained with the tag mode and the control mode are subjected to difference calculation for each pixel between these images. As a result, information with regard to blood flowing into the imaging slab, i.e., an ASL image indicating circulation can be obtained.

Attempts to quantify flow (perfusion) using the above-described ASL imaging are known. An example thereof will be described.

In general, the flow f is obtained from the equation which is referred to as the Bloch equation. (See "MRM 35: 540-546 (1996), C. Scwarzwauer et al", for example.) The longitudinal (lattice-spin or T1)-relaxation Bloch equation, which is usable when there is a flow "f," is represented with Expression (a).

$$dM/dt = (M_0 - M)T1 + f \cdot (M_a - M/\lambda) \quad (a)$$

wherein $\lambda$ is the cerebral blood flow distribution coefficient of water (0.9 to 1), wherein M is the pixel value of the tissue image, wherein $M_a$ is the longitudinal magnetization density, wherein $M_0$ is the pixel value of tissue image under saturation (proton density image), and wherein T1 is the tissue T1 (longitudinal or spin-lattice) relaxation time value.

Also, the following expression holds.

$$1/T1_{app} = 1/T1 + f/\lambda \quad (b)$$

wherein T1app is the apparent T1.

Thus, images are obtained with the tag mode and the control mode, respectively, whereby the flow f is calculated. That is, $M_0$ and T1 are measured for each pixel, and reckoning T1 in blood (which is equal to $T1_a$: the suffix "a" indicates artery) to be the same as T1 in tissue, it has been reported that the flow f is represented with the following expression.

$$f \propto \lambda \cdot \Delta S / \{2 \cdot TI \cdot M_0 \cdot \exp(-TI/T_{app})\} \quad (c)$$

wherein $\Delta S$ is the pixel value ($= S_{cont} - S_{tag}$) of the ASL image, and wherein TI is the inversion time.

However, in practice, there is the need to measure $M_0$ and T1 for each pixel for calculating the flow f according to the above-described Expression (c), so measurement is troublesome, a great amount of data is required, and also the calculation amount is great, leading to an increase in calculating time.

Furthermore, it is known that due to a great number of image data sets containing time difference in acquisition, being used, misregistration or the like occurs due to the body motion, and accordingly, deterioration of measurement precision is caused due to the margin of error occurring from this point.

As described above, there are various problems encountered when applying the conventional flow (perfusion) quantification method to clinical practice, so quantification wherein these problems are solved and practical use can be made is desired. In particular, in the event of applying the method to a patient affected with acute stage infarction, there is the need to easily and quickly quantify flow.

Taking the above-described situation into consideration, a method wherein the gathered data obtained from an imaging slab with ASL imaging can be kept to a minimum, and linear scaling is performed using the gathered data, thereby easily quantifying flow (perfusion) on an imaging slab, is proposed in Japanese Unexamined (Laid-open) Patent Application Publication No. 11-375237.

However, the flow quantification method disclosed in the aforementioned application is a method which is related to the "single-compartment model", upon which the Bloch equation is based. The single-compartment model is based upon an assumption that water, which is a tracer for ASL, has the nature of complete diffusion. That is, the single-compartment model is based upon a precondition that the water spins in artery blood flow transported to tissue are rapidly transferred into the tissue and the spins of water in the artery blood provide T1 values of the tissue.

However, in practice, such conditions are never satisfied completely during the time period from labeling of upstream artery blood flow up to the beginning of data acquisition (a time period TI (in practice, around one to two seconds)). The reason is that the number of the water spins left on the capillary vessel bed is greater than that of the water spins outside the capillary vessel. Accordingly, the above-described quantified flow value readily contains a margin of error due to the preconditions not being satisfied completely, upon which the single-compartment model is based, and accordingly, a flow quantification method with higher precision is desired.

On the other hand, study with regard to a model with higher precision as compared with the single-compartment model is being undertaken as shown in the document "Jinyuan Z, David A W, Peter C M: Two-compartment model for perfusion quantification using Arterial Spin Labeling, Proc. Intl. Soc. Magn. Reson. Med., 2000; 8, 166". However, the more complex the model becomes, the greater the number of parameters required for the flow quantification is, leading to calculation being more complex.

On the other hand, in experiment, it has been reported that the ASL signal intensity approximately linearly correlates to the blood flow in experiments on animals and so forth.

SUMMARY OF THE INVENTION

The present invention has been made taking a flow quantification method based upon the above-described conventional ASL method into consideration, and it is an object of the present invention to provide a flow quantification method wherein flow values with high precision more precisely reflecting the actual behavior of flow (perfusion) can be obtained with small calculation amounts.

First of all, terms in the present invention will be defined.

While "flow" is generally obtained by placing an imaging slab in the brain, and more properly indicates "CBF" (cerebral blood flow), the value is a value which can be applied to internal organs other than the head, as well, so the term is used for indicating tissue blood flow (regional blood flow), which is referred to as flow "f" [ml/100 cc/min], as a generalization. "Flow quantification" indicates obtaining of quantification information with regard to flow (blood flow and so forth) for each pixel, including an arrangement wherein images of blood flow are displayed as flow images.

According to the present invention, quantification information with regard to flow (perfusion) can be obtained by performing conversion based upon linear scaling or a higher-order equation for an ASL image in principle, obtained based upon the ASL method, noninvasively without using a contrast medium. The scaling values used in the scaling, or the values used in the conversion, are calculated beforehand, or are calculated from the image values of the reference phantom for each time.

Description will be made below regarding results of the simulations and experiments, performed by the present inventor for realizing a simple and highly precise flow quantification according to the present invention. The simulations and experiments present grounds for quantification of local brain blood flow in the ASL imaging.

[I] Simulation

[A] Purpose of Simulation

It is an object of the simulation to realize simple and quantitative ASL imaging which can be used in clinical applications, and using the two-compartment model which is thought to be relatively close to the model wherein water is a tracer in the ASL. Theoretical study was made for the relation between the signal intensity of the ASL (PASL) image with the pulse method and blood flow or other parameters, while comparing with other modalities such as the Cold Xenon-CT (Xe-CT), Positron Emission CT (PET), and the like. Furthermore, in the simulation, correlation was made between an Xe-CT image and an image obtained with the PASL method (PASL image), on the head of volunteers, and the validity of the idea of the present inventor that simple scaling can be performed based upon the relation between the ASL signals and the CBF obtained during a single time period TI was studied from the experimental point of view, as well.

[B] Method for Simulation (B1) Model

FIG. 1 illustrates the two-compartment model used in the simulation, and definitions of the parameters employed in the model will be described below.

$Q_1/Q_2$ indicates (the tracer amount in the compartment within blood vessels)/(the tracer amount in the compartment outside blood vessels), $Q_t$ indicates the sum of the tracer per unit voxel ($Q_t = Q_1 + Q_2$), $V_1/V_2$ indicates (the volume of the compartment within blood vessels)/(the volume of the compartment outside blood vessels) (note that $V_1 + V_2 = 1$), $C_a$ indicates the tracer concentration in the artery blood flow (input function into the model).

"f" is the blood flow per unit,

PS is the Permeability Surface Area Product of Water (the amount of a tracer permeating from the inside of blood vessels to the outside thereof per unit time, which will be indicated with [ml/100 cc/min]), $T1_i/T1_e$ indicates the (T1 relaxation time for the compartment within blood vessels)/(T1 relaxation time for the compartment outside blood vessels), "$\lambda$" indicates the blood-tissue distribution coefficient (i.e., $\lambda = M_{oe}/M_{oi}$, wherein $M_{oi}$ indicates the longitudinal magnetization density of the water within blood vessels in the stationary state, and $M_{oe}$ indicates the longitudinal magnetization density of the water outside blood vessels in the stationary state), and "t" indicates the time period following the labeling (which is equal to TI).

With each compartment, making description based upon the Fick principle, which states that the tracer amounts, $dQ_i$ and $dQ_e$, left during a minute time period dt are differences between the entering tracer and the exiting tracer during the minute time period dt; the changes in the tracer for each compartment amount over time can be represented by the following expressions.

$$dQ_i/dt = fC_a - (f/V_i)Q_i + (PS/(\lambda V_e))Q_e - (PS/V_i)Q_i - (1/T1_i)Q_i \quad (1)$$

$$dQe/dt = (\lambda PS/V_i)Q_i - (PS/V_e)Q_e - (1/T1_e)Q_e \quad (2)$$

The expressions are solved with regard to $Q_i$ and $Q_e$, whereby $Q_t = Q_i + Q_e$, which is the total tracer amount per unit voxel, proportional to the tracer signal intensity, is obtained.

While, water is employed as a tracer with the ASL imaging, water does not serve as a diffusion tracer, and the PS, which represents the degree of the tracer transferring from vessels to tissue, is finite, and accordingly, a unit voxel is divided into two compartments of the inside of blood vessels and the outside of blood vessels. The ASL is similar to a case of using a water tracer, $H_2^{15}O$ in the PET. However, while with the water tracer in the PET, the relaxation time is long, around two minutes, so the state can be considered uniform within the two compartments, with the ASL imaging, the relaxation time is short, in the order of seconds, and the states are different between the inside of blood vessels and the outside of blood vessels, complicating the model as compared with the PET.

Cold xenon used in the Xe-CT, which has been analyzed with the single-compartment model, can be regarded as a diffusion tracer in measurement time in the order of several minutes, and has no relaxation. With the Xe-CT or the PET, a tracer is injected by inhalation or injection in a jugular vein, accordingly, with the input function $C_a(t)$, the response function in tissue is influenced by the lungs. On the other hand, with the ASL, $C_a(t)$ with regard to the artery vessels is directly provided to the artery vessels in the brain by the RF. Ignoring the difference in λ within these parameters in the two-compartment model shown in FIG. 1, the tissue models for the Xe-CT, PET, and ASL can be represented by the two-compartment model with $T1_a$, $T1_i$, $T1_e$, and PS being different, for each case.

(B2) Conditions

With the object as blood flow in tissue in the brain, representative parameters are defined for gray matter (GM) and white matter (WM). Note that, with both parameters, the delay time for the tracer reaching the tissue of interest is ignored, (i.e., τd=0) and $C_a(t)$ is a concentration relative to a tracer concentration in the equilibrium with $T1_i$ and $T1_e$ being infinite and PS being infinite. And an assumption is made that $C_a(t)$ for the PET and the Xe-CT, though different from the actual case, is set such that a tracer is directly injected to the artery in a step-function manner for comparing $Q_t(t)$ in the tissue with the ASL. Furthermore, an assumption is made that the signal intensity (ASL signal) per unit voxel in the ASL image is proportional to a tracer concentration, i.e., the tracer amount per unit voxel.

Specifically, with $V_i$=0.03 (CBV=3%), f=80[ml/100 cc/min] (for GM), and f=20[ml/100 cc/min] (for WM) as common parameters, generalizing the input function, an assumption was made as described below (see FIG. 2A).

$$C_a(t)=A\cdot\exp[-t/T1_a] \text{ (for } \tau_d<=t<T_{tec}+\tau_d)$$

$$C_a(t)=0 \text{ (for cases except for the above)} \quad (3)$$

Wherein "A" indicates the coefficient representing the labeling effect, wherein $T1_a$ indicates the T1 relaxation time for artery blood in labeled portion, wherein $\tau_d$ indicates the delay time for a tracer being transmitted from the artery input function measurement portion to the tissue of interest (transmit delay time), and wherein $T_{tec}$ indicates the labeling time width (tag duration time).

The parameters are set for each of the Xe-CT, PET, and PASL, as described below based upon the above-described assumption.

(a) In the Case of Xe-CT

The parameter A is set to 1, the parameters $T1_a$, $T1_i$, and $T1_e$ set to infinity, the parameter PS is set to infinity, the parameter λ is set to 1, the parameter $\tau_d$ is set to 0, and the parameter $T_{tec}$ is set to infinity.

In this case, from Expression (1) and Expression (2), the following simplified expression can be obtained.

$$dQ_t/dt=f(C_a-C_v)=f(C_a-C_t/\lambda) \quad (4)$$

wherein $C_v=Q_t/V_i$.

(b) In the case of PET using water ($H_2^{15}O$), A is set to 1, $T1_a$, $T1_i$, and $T1_e$ are set to 120 sec, PS is set to 130 [ml/100 cc/min], λ is set to 1, $\tau_d$ is set to 0, and $T_{tec}$ is set to infinity.

(c) In the case of PASL, A is set to 1, $T1_a$ and $T1_i$ are set to 1.2 sec, $T1_e$ is set to 0.7/0.9 (WM/GM) sec, PS is set to 130 [ml/100 cc/min], λ is set to 0.82/0.98 (WM/GN)[16], $\tau_d$ is set to 0, and $T_{tec}$ is set to infinity.

[C] Details of the Simulation

Expression (1) and Expression (2) were solved, and study as described below was performed.

(C1) Change in the Tracer over Time for Each Modality:

The change in the tracer amount in the compartments corresponding to the inside and outside of blood vessels, and the total tracer amount, over time, were researched for three types of methods of the PASL, PET using water tracer, and Xe-CT.

(C2) Relation Between the Tracer Signal Intensity (ASL Signal) and the Blood Flow "f"

Reckoning the parameters other than the blood flow f to be constant, with the PS indicating vessel permeability as a parameter, comparison was made between the single-compartment model (corresponding to a case wherein PS is infinite) and the two-compartment model, in order to investigate how far the tracer signal intensity correlates to the real blood flow f. Note that, the single-compartment model corresponds to the two-compartment model with PS set to infinity.

(C3) Change in the Tracer Signal Intensity Due to the Fluctuation of the Parameters:

With regard to brain tissue, investigation was made how far the margin of error occurred due to the assumption that the parameters in the model which were not measured for each measurement were constant. Based upon the conditions for GM, and with PS as a parameter, investigation was made with regard to the relation between the tracer signal intensity, the T1 relaxation time $T1_e$ outside a vessel, $V_i$ indicating the blood flow, and the blood-tissue distribution coefficient λ for a tracer. Furthermore, as shown in FIGS. 3A and 3B, investigation was made with regard to the relation between the delay time τd, the parameter Tτc, and the tracer signal intensity, depending upon the presence or absence of the pre-saturation pulse (which will be referred to as Presat (Tag End Cut (TEC))) which was provided to the tag portion after the labeling time width $T_{tec}$ following application of the tag IR pulse (Tag-IR) which was used for reducing vessel signals.

(C4) CBF Quantification with the Linear Scaling Method:

With the tracer signal intensity ($Q_t$) obtained by providing the parameters for GM and WM based upon the two-compartment model as a theoretical value, the CBF yielding the same tracer signal intensity as the theoretical value was calculated with the single-compartment model and the linear scaling method.

With the linear scaling method, the constant k in Expression (5) was obtained using collinear approximation for two points of theoretical values for WM and GM, and CBF was calculated with Expression (6).

$$\text{ASL signal}=k\cdot\text{CBF} \quad (5)$$

$$\text{CBF}=K\cdot(\text{ASL signal}), \text{ wherein K is } 1/k. \quad (6)$$

[D] CBF Quantification with the Linear Scaling Method from Measurement Data in the PASL and the Xe-CT (D1) Measurement subjects were nine normal volunteers wherein imaging was performed with the same slices in the Xe-CT and the PASL on the same day (D2) With the ASL imaging, a 1.5-T MRI apparatus manufactured by Toshiba corporation was employed. Specifically, imaging with the PASL method was performed with the ASTAR (modified STAR using Asymmetric Inversion slabs) method. The ASTAR method was adaptation of the EPISTAR method (see the document "Edelman RR et al.: Qualitative mapping of cerebral blood flow and functional localization with echo-planar MR imaging and signal targeting with alternating radio frequency, Radiology 1994; 192: 513-520) as shown in the document "T. Kimura: Noninvasive blood flow imaging with modified STAR using asymmetric inversion slabs (ASTAR) method, Japanese Journal of Magnetic Resonance in Medicine, 2001; 20(8), 347-385". That is to say, the ASTAR method is a method wherein the control portion and the tag portion are spatially and asymmetrically placed so as to reduce the unnecessary blood vessel signals within veins, flowing from the apex, while canceling the MT effect.

Also, imaging was performed with reception gain being fixed with the transmission/reception QD coil for the head, under the imaging conditions of the 2D Fast Gradient Echo (FFE) method (TR/TE/FA=9 ms/3.6 ms/15 deg, TI=1400 ms, FOV=25.6 cm, slice thickness=10 mm, single slice), tag thickness of 10 cm, slice-tag gap of 1 cm, and $T_{tec}$ of 800 ms. FIG. 3A is a schematic diagram which illustrates the sequence, and FIG. 3B illustrates imaging positions for each slab. The ASL signals of the obtained ASL image are absolute values of the difference between signals of the tag image and the control image, i.e., the signal intensities of inflow blood.

(D3) Xe-CT: A total of nine scan images wherein measurement was made with the CT using the short-time inhalation method (wash-in/wash-out protocol) with inhalation of 30%-Xenon gas for 3 minute, one minute each for each eight minutes, were used.

(D4) Analysis: ROIs with the same size and symmetric positions were set to the cortex of frontal lobe, white matter of frontal lobe, thalamus, cortex of occipital lobe, and white matter of occipital lobe, and average values were measured.

The proportional constant k is obtained by calculating Expression (5), collinear approximation passing through a point (0,0), based upon the relation between the Xe-CT CBF and the ASL signals in the same way as with the simulation. Subsequently, with K as 1/k, scaling was performed for the ASL signals with Expression (6), and thus converted into the CBF values. Note that white matter of frontal lobe, cortex of occipital lobe, and thalamus, were used for calculating the correlation coefficient (the number of the subjects N was nine, and the number "n" of ROIs was 54 (9×3×2)). Furthermore, averages and SDs were each calculated for the Xe-CT CBF and ASL CBF for each tissue unit, and comparison was made between the Xe-CT CBF and the ASL CBF for the averages and SDs. Also, the Xe-CT CBF image and ASL CBF image were displayed with the same scaling. Note that smoothing filtering processing was performed for the Xe-CT image so as to be displayed with the same resolution as the ASL CBF image.

[E] Results (E1) FIGS. 3A and 3B Illustrates the Change in the Tracer Signal Intensity (ASL Signal) Over Time for Each Modality.

(a) Case of Xe-CT: in the Event of a Tracer being Diffusive and Having No Relaxation (in the Case of PS>>f, $T1_i=T1_e=\infty$):

While in this case, the tracer signal intensity (ALS signal) increases in an exponential manner over time, and reaches a balance in around three minutes, as shown in FIG. 4A, the tracer signal intensity can be regarded as being in an approximately linear relation with time in the range of a short time (less than 10 sec). The ratio of the tracer amount within blood vessels as to that outside blood vessels is the same as the volume ratio of the volume within blood vessels as to that outside blood vessels. That is to say, the relation $Q_i/Q_e=V_i/V_e$ holds.

(b) Case of PET Using Water ($H_2^{15}O$): Case of a Tracer being Water Having Small Relaxation (PS Approximately the Same as f, $T1_i=T1_e>>t$):

As shown in FIG. 4B, while the tracer amount within blood vessels is less as compared with that outside blood vessels immediately following injection of a tracer, the tracer amount increases over time, becomes the same as that outside blood vessels in around two seconds, and at a balance point, the tracer concentrations inside and outside blood vessels become the same, whereby the ratio of the tracer amount within blood vessels as to that outside blood vessels becomes close to the ratio of the volume within blood vessels as to that outside blood vessels ($Q_i/Q_e \rightarrow V_i/V_e$). Thus, a balance is formed for the inside and outside of blood vessels in the order of measurement time for the PET.

(C) Case of PASL: Case of a Tracer being Water Having Great Relaxation (PS Approximately the Same as f, $T1_i=1.2$ s, $T1_e=0.9$ s):

Measurement results in this case are shown in FIG. 4C. Due to the ASL with the MRI having relaxation greater than water with the PET by one order or more, and the PASL having the nature of the tracer signal intensity having a peak at around t=1 sec, there is the need to determine the measurement time so as to be 2 second or less, however, a balance is not formed for the tracer concentration at this point in time, and accordingly, the ratio of the tracer outside blood vessels is less than that within blood vessels ($Q_i/Q_e>V_i/V_e$).

(d) Case of the PASL with PS Equal to Infinity, and Other Conditions Being the Same as with (c)

The conditions correspond to the single-compartment model with PS being equal to infinity, i.e., with the single-compartment model making an assumption that a tracer is uniformly diffused within a voxel, and accordingly, components outside blood vessels occupy almost all the voxel in short time. As shown in FIG. 4D, the tracer signal intensity is somewhat greater than a case of using PS close to the actual value.

(E2) Relation Between the Tracer Signal Intensity and the Blood Flow f:

FIG. 5 illustrates a curve for the change in the tracer signal intensity (ASL signal) with regard to the blood flow f with PS at t=1.4 s as a parameter.

In the event of PS is far greater than f, the single-compartment model can be employed for approximation, and in the event that the measurement time t is fixed following the labeling (in a case of the PASL, t is fixed to be 1 to 2 sec), the tracer signal intensity is proportional to the flow f. On the other hand, in the event of PASL employing the two-compartment model, the less PS is, the less the tracer signal intensity with a high flow is. As a result, as shown in FIG. 5, the tracer signal intensity exhibits a property curve projecting upwards. However, the tracer signal intensity ASL signals and the flow f have an approximately proportional relation therebetween in the range of brain blood flow of 0 to 100 [ml/100 cc/min]. Note that the relation holds under the conditions of $T1_e$ for GM, and accordingly, $T1_e$ of the ASL signals from WM is less than that from GM, the maximal value, wherein the proportional relation holds, is somewhat small.

(E3) Relation Between the Tracer Signal Intensity and other Parameters with the ASL:

(a) The Relation Between the Tracer Signal Intensity and the T1 Relaxation Time Outside Blood Vessels $T1_e$:

As shown in FIG. 6A, while the greater PS is, i.e., the greater the permeability to the outside of blood vessels is, the greater the change in the tracer signal intensity (ASL signal) with regard to the change in $T1_e$, due to increase of the ratio of the tracer component $Q_e(t)$ outside blood vessels as to the tracer component Qi(t) within blood vessels, with tissue in the brain (PS=130 [ml/100 cc/min]), in the event of t being 1.4 sec, for example, the tracer signal intensity is reduced only by approximately 5% even in the event of making an assumption that $T1_e$ for GM is the same as $T1_e$ for WM, however, with the single-compartment model with PS as infinity, the tracer signal intensity changes by 17%.

(b) Relation Between the Tracer Signal Intensity and the Volume of the Blood Vessel Bed $V_i$:

As shown in FIG. 6B, in the ASL with PS of 130 [ml/100 cc/min], while the tracer signal intensity (ASL signal) is somewhat reduced with $V_i$ less than 0.02, the tracer signal intensity changes little with $V_i$ greater than 0.03. The tracer signal intensity change around 20% with $V_i$ in the range between 0.02 and 0.05, which is thought to be the range for the human brain.

In general, in the event that PS is far greater than f, and relaxation is uniform for the outside and inside of blood vessels, contribution of $V_i$ contained in the entire signals is simply $V_i$, and is constant over time ($Q_i(t)/Q_t(t)=V_i/V_t$). That is, the total of the tracer amount per unit volume is constant even in the event that $V_i$ changes. However, in the event of PS generally the same as f as with PET with water and ASL, the total sum of the tracer amount per unit volume changes over time, and becomes close to the volume ratio in the stationary state ($Q_i(t)/Q_t(t) > V_i/V_t$, in the event of a short t: $Q_i(t)/Q_t(t) \rightarrow V_i/V_t$, in the event of t of infinity)

The shorter the time period following injection of the tracer is, and the smaller PS is as compared with f, the greater the ratio of the tracer being left within blood vessels is. Accordingly, contribution of signals within $V_i$, which is the volume of the blood vessels, increases. As shown in FIG. 4C, with the measurement for ASL, at the measurement point in time in the range between 1 and 2 sec, half or more of the entire signals are due to $V_i$, even in the event of $V_i$ being around 0.03.

(C) Relation Between the Tracer Signal Intensity and the Blood-Tissue Distribution Coefficient $\lambda$:

As shown in FIG. 6C, the greater PS is, the relatively greater the signal component $Q_e$, for the outside of blood vessels becomes, so the change in the tracer signal intensity (ASL signal) due to the change in the blood-tissue distribution coefficient $\lambda$ for the tracer increases. The tracer signal intensity obtained with an assumption of $\lambda$ being 1 is $(Q_i+Q_e)/(Q_i+\lambda Q_e)$ times as large as the tracer signal intensity obtained using a true value for $\lambda$. With the $\lambda$ for water in GM and WM as 0.98 and 0.82, respectively, and taking $\lambda$ as 1, there is little problem for GM, and with WM, the tracer signal intensity is over-evaluated by the margin of error of 6% at t=1.4 sec, around 1.2 [ml/100 cc/min] with CBF conversion.

(d) Relation Between Tag End Cut (TEC) Parameter and the Tracer Signal Intensity:

FIG. 7A illustrates the change in the tracer signal intensity (ASL signal) over time for GM with regard to the presence or absence of using Tag End Cut (TEC), and FIG. 7B illustrates the relation between the tracer signal intensity and the delay time $\tau_d$ for both GM and WM at t=1.4 sec.

In the event of setting the measurement point in time to $t > T_{tec} + \tau_d$, with a case of applying TEC, the tracer signal intensity is reduced as compared with a case of not applying TEC, but the influence due to the delay time $\tau_d$ is reduced. The reason is that relaxation is not influenced by the delay time $\tau d$, and begins immediately following labeling (t=0), and accordingly, signal reduction due to relaxation is dominant. The time parameter t with regard to TEC should be determined so that the expression $t > T_{tec} + \tau_d$ is satisfied with $T_{tec}$ which is a time width sufficient for labeling artery blood filling Vi, and with maximal $\tau d$ in the measurement system. In the event of not applying TEC, the state with the same conditions as with the case of applying TEC can be obtained at around t=2.5 sec. However, an arrangement wherein TEC is applied has the advantage of the measurement time being reduced as compared with an arrangement wherein TEC is not applied. Also, in the event that the delay time $\tau d$ cannot be ignored, signals are not detected in the tissue portion in the range of $t < \tau_d$. In practice however, in this case, labeled blood continues to pass through arteries, readily leading to occurrence of vessel artifacts accompanying a high signal rate. Such situations can be suppressed by applying TEC.

(e) Comparison Between Tracer Signal Intensity and CBF Values Obtained with Linear Scaling Method and other Models FIG. 8 illustrates the relation between CBF values and the tracer signal intensity (ASL signal) for each model. Table 1 in FIG. 9A shows CBF values wherein taking the tracer signal intensity calculated based upon the two-compartment model for each of WM and GM as the theoretical values, and the same tracer signal intensity as the theoretical values are calculated from the CBF values based upon each method.

With the single-compartment model, even in the event of providing real parameters other than PS, the calculated CBF value is greater than the theoretical value by 44% in WM, and is less by 6% in GM, in particularly, the margin of error is great for WM. That is due to over-evaluation with regard to the component outside blood vessels due to the assumption that PS is infinity. In the event of employing the linear scaling method, the calculated proportional coefficient k is $5.543 \times 10^{-5}$, K=1/k=18041, and the calculated CBF value is greater as compared with the theoretical value by 6% for WM, and is less by 0.4% for GM, which is sufficient for practical use.

(E4) Evaluation of the Linear Scaling Method Using Measured Data:

As shown in FIG. 10, the tracer signal intensity and Xe-CT CBF (ASL signal) correlate one to another excellently.

The following relation was obtained.

ASL signal=2.43·(Xe-CT CBF)+42.39, correlation coefficient $r=0.803 (P<0.001)$, n=54)

Also, with collinear approximation passing through the origin (0, 0), the following relation was obtained.

Mathematical Expression 8

ASL signal=3.33·(Xe-CT CBF), $r=0.768 (P<0.001)$

Accordingly, the proportional coefficient K=1/k=0.3 was obtained, and ASL CBF was obtained by multiplying ASL signal intensity by the coefficient, whereby the relation between the ASL CBF and the Xe-CT CBF was obtained as shown in FIG. 11. The CBF values corresponding to the relation are shown in Table 2 in FIG. 9B. Also, though not shown in the drawings, the standard deviation for the thalamus was great in particular as compared with other tissue for both images with image examples for the Xe-CT CBF and the ASL CBF, but the fluctuation of the ratio SD/MEAN for each tissue was around 20%.

Furthermore, with the PASL image obtained with the tag time width $T_{tec}$ using the Tag End Cut as a parameter, not shown in the drawings, blood signals flowing from the lower-limb side is markedly reduced in the middle cerebral artery, the cerebellum, and the thalamus, accompanying reduction of $T_{tec}$.

[F] Consideration

[F1] Difference Between the Single-Compartment Model and the Two-Compartment Model:

The single-compartment model corresponds to a model wherein following a tracer reaching, a balance is immediately reached within a voxel, that is to say, the single-compartment model corresponds to the two-compartment model with PS indicating the blood-vessel permeability being infinity, and relaxation being constant. On the other hand, with the tracer signal intensity (ASL signal) obtained from an actual apparatus based upon the two-compartment model, in the event that the flow f is not great, with G as the proportional coefficient depending upon the measurement system such as a gain of the transmission/reception system, using the above-described parameters, k in Expression (5) can be represented with the following Expression.

$$k = GAM_{0i} \cdot \text{function}(T1_i, T1_e, \lambda, V_i, PS, t, \tau_d) \quad (7)$$

In the event of employing the single-compartment model for approximation, k can be represented with following expressions.

$$k = 0 \text{ (in the event of } t < \tau_d)$$

$$k = GAM_{0i}/\lambda(t - \tau d)\exp[-t/T1_e] \text{ (in the event of } \tau_d < t < \tau d + T_{tec})$$

$$k = GAM_{0i}/\lambda T_{tec}\exp[-t/T1_e] \text{ (in the event of } \tau_d + T_{tec} < t) \quad (8)$$

In the event of $GAM_{0i}/\lambda$ being 1, the same scale as with the simulation is obtained. With the relation between the tracer signal intensity (ASL signal) and the flow f, with PS as a parameter, as shown in FIGS. 4A through AD, the tracer signal intensity for a total of the tracer signal intensities within and outside blood vessels is not greatly influenced by the change in PS of the tracer under conditions for the human brain in a case of the PASL, fortunately. Thus, in the event of employing the PASL method, calculations based upon the single-compartment model wherein PS is far greater than f does not cause a great margin of error, at least for the human brain.

The present inventors studied simulation based upon the two-compartment model which is closer to practice as compared with the other models, and it has been found that the influence of the difference in T1e or λ, regarding which it has been thought that there is the need to measure in the event of employing the single-compartment model, is relatively small due to contribution of the component outside blood vessels being small, and contribution of the blood vessel bed volume (CBV), which has influence in the two-compartment model, is small as compared with the margin of error of 3% or more under conditions of parameters for the human brain with the PASL, as shown in FIG. 5. Accordingly, making an assumption that these parameters are constants does not cause a great margin of error, so there is little need to measure these parameters. Conversely, in the event of measuring these parameters and correcting T1 relaxation based upon the single-compartment model, the correction results in over-correcting, so measurement is unnecessary.

On the other hand, the input function for the ASL (CASL) employing continuous RF wave for labeling corresponds to Expression (3), which represents $C_a(t)$, with τd being substituted for t (see the waveform of the input function shown in FIG. 2B), in the simulations which was performed separately, the ratio of the component within blood vessels as to that outside blood vessels $Q_i/Q_t$ was around 60% in the stationary state, and the change in the tracer signal intensity depending upon the fluctuation of the parameters of $T1_e$, $V_i$, and λ is generally the same as with the PASL.

In the event of measuring the parameters other than the tracer signal intensity for correction, over-correction results with the single-compartment model for both PASL and CASL, so in this case, the two-compartment model should be employed. Note that while an assumption is made for both models that following the tracer reaching, the tracer concentration immediately becomes uniform in each compartment, the tracer signal intensity is robust with regard to PS determining the tracer amount within and outside blood vessels, and accordingly, the influence of the assumption is thought to be small.

[F2] Potential for Proportional Conversion from the Tracer Signal Intensity into the Blood Flow f:

It has been found by simulation based upon the two-compartment model that the tracer signal intensity (ASL signal) measured at the fixed measurement point in time is proportional to the blood flow f, and is robust in the range of the human brain with regard to the influence of the parameters which may change, such as $T1_e$, $V_i$, λ, PS, and the like.

On the other hand, with measured data, an excellent correlation has been confirmed between the tracer signal intensity obtained with the PASL method and the Xe-CT CBF data which is obtained with the established quantification method, and it has been confirmed that an approximately linear relation holds between the tracer signal intensity obtained with the PASL method and the Xe-CT CBF data, as shown in the above-described simulations. Thus, it has been found that once the proportional coefficient K for converting the tracer signal intensity (ASL signals) into the CBF value is obtained with any method, the tracer signal intensity can be converted into the CBF value.

The coefficient G in Expression (7) representing k, which is a parameter depending upon the measurement system, is valid so long as the apparatus and image conditions are the same, so there is no need to measure the coefficient G for each time, and the change in the gain of the transmission/reception system is thought to be corrected by measuring the signal intensity for the brain tissue or a static phantom under the condition of the present apparatus system.

The change in the average (SD/MEAN) of the overall control images on the subjects, which were employed in this analysis, was around 6%. Due to employing the same slice level, it is thought that the influence of the gain of the transmission/reception system G can be ignored. However, the influence of the gain G can be reduced even in the event that the coil sensitivity is not uniform. That is, the signal intensity $S_0(=G \cdot M_{0i})$ proportional to the longitudinal magnetization density $M_{0i}$ is measured in the control image wherein TI is sufficiently long so that normal white matter, which can be regarded as having the same proton density as blood, employed instead of blood which is the object of measurement due to the general difficulties of measurement of blood in the aforementioned long TI, is generally in the stationary state, and the relative signal intensity ALS signal/$S_0$ is employed, so the transmission/reception-system gain G and $M_{oi}$ are cancelled, that is to say, a more universal coefficient is obtained.

It is needless to say that the conversion from the tracer signal intensity into the blood flow f is not restricted to simple scaling. An arrangement may be made wherein a table is compiled with regard to the relation between the blood flow and the tracer signal intensity, and the blood flow f is obtained from the tracer signal intensity using the table, and thus quantification can be performed even if the blood flow and the tracer signal intensity have a non-linear relation.

In a case that signals obtained from the inside of the blood vessels which serve a pathway for the labeled blood can be ignored, in the event of not employing TEC, the reduction of the tracer signal intensity is caused due to the extension of the delay time τd, and even in the event of employing TEC, the tracer signal intensity slightly increases due to extension of the delay time τd. In the event that the change in the tracer signal intensity is uniform within the slice face, the tracer signal intensity can be converted with the same scaling values. While it has been reported that the delay time τd in white matter is extended by around 0.5 sec as compared with gray matter, it is thought that the margin of error due to the delay time τd can be reduced with PASL method using the Tag End Cut by setting the condition of TI−$T_{tec}$>τd. Note that in the experiments, a single slice was used for reducing the delay time τd as possible, and the gap between the tag slab and the image slab was made narrow, around 1 cm, and accordingly, the relation, TI−$T_{tec}$=1.4−0.8=0.6 sec, is obtained, and thus the difference between the delay time τd in GM and WM can be generally ignored.

Next, regarding the influence of vein signals, with the mean transit time of blood in tissue as MTT, in the event of t being greater than MTT, the ratio of the labeled water reaching veins increases, and consequently, contribution of vein signals might occur in a voxel. However, in the human brain, it is known that MTT is around 2 to 5 sec, and the blood signal is reduced according to the function of exp[−t/$T1_a$], and accordingly, it is thought that the influence of vein signals can be ignored under conditions of t being less than 2 sec for PASL. The influence of blood vessel signals directly flowing into the imaging slab for blood flow from the apex can be regarded to be generally from the vein component for the head, and accordingly, the influence can be reduced by using the ASTAR method wherein only the blood flow from the legs are labeled instead of using the EPISTAR method or the FAIR method, or by using the Tag End Cut providing the delay time following labeling, thus suitably setting parameters.

As described above, the simulations using the two-compartment model, which is a more highly precise model, are provided, and in the simulations, it has become clear that a) the tracer amount (tracer concentration) Qt is robust with regard to the parameters ($T1_e$, λ, $V_i$(CBV), PS) other than the flow (i.e., Qt is approximately represented by the function with regard to only the flow f), b) the flow can be obtained with an approximately linear approximation even just by using TI in the range of the order of the brain blood flow (which is less than 100 [ml/100 cc/min]) (i.e., the proportional relation, $Q_t$=K·f approximately holds: wherein K is the proportional coefficient), c) furthermore, approximation with a quadratic equation further improves precision of the approximation (i.e., the approximation equation, $Q_t$=a·f$^2$+b·f is further preferably employed).

[II] Experiments

The present inventor performed experiments separately in order to investigate a simple conversion method for performing converting from the tracer concentration to the flow f with the ASL method.

The flow f was calculated under various conditions (#2 through #7: difference in model and $T1_e$, and scaling for linear conversion) with the tracer concentration $Q_t$ in a case of inputting real parameters (#1) as the standard, for each of gray matter (GM) and white matter (WM) with regard to the T1 relaxation time $T1_e$ for each compartment outside blood vessels using the two-compartment model (see FIG. 12).

The real parameters will now be described.
In the event of WM:
CBF=20, PS=130, $V_i$=0.03, $T1_e$=0.7 s, λ=1
In the event of GM:
CBF=80, PS=130, $V_i$=0.03, $T1_e$=0.9 s, λ=1.

FIG. 13 and FIG. 14 illustrate conversion expressions wherein approximation is performed with the origin (0, 0) and the theoretical value sets of the flow f and the tracer concentration Qt for WM and GM (3 points including the origin) with a linear equation and a quadratic equation. FIG. 13 illustrates a case of the PASL method, and on the other hand, FIG. 14 illustrates a case of the CASL method.

As can be found from the results, while the theoretical values of WM with linear approximation (y=kx) has some margin of error, in the event of employing approximation using a quadratic equation (y=ax$^2$+bx), the margin of error is reduced. That is to say, it is known that the greater the value of the flow f is, the proportional relation between the tracer concentration $Q_t$ and the flow f is further deteriorated, and the relation exhibits a curve more protruding in the upper direction. Accordingly, it has been found that in the event of the flow f of high value, better approximation can be made for the two-compartment model using conversion with a higher-order equation such as a quadratic equation as compared with a linear equation.

The present invention is configured as described below based upon the information obtained from the above-described simulations and experiments.

Practically, as one aspect, the present invention provides an MRI (Magnetic Resonance Imaging) comprising: imaging means for performing a scan in accordance with an ASL (Arterial Spin Labeling) technique on a region to be imaged of a subject to be examined so that image data is acquired from the region to be imaged; storing means for storing therein pieces of information indicative of a relationship between a concentration of tracer served by water and a flow of perfusion indicative of blood flow (i.e., microcirculatory blood flow) in the tissue, the relationship being obtained based on a model that uses at least two compartments placed inside and outside of a flow of blood that diffuses into the tissue of the region to be imaged and that considers temporal changes in the diffusion of the blood flow into the tissue; and quantifying means for quantifying the perfusion in the region to be imaged by giving an amount derived from the image data to the relationship information between the tracer concentration and the flow of the perfusion.

As another aspect, the present invention provides An MRI (Magnetic Resonance Imaging) comprising: an imaging unit configured to perform a scan in accordance with an ASL (Arterial Spin Labeling) technique on a region to be imaged of a subject to be examined so that image data is acquired from the region to be imaged; a storing unit configured to store therein pieces of information indicative of a relationship between a concentration of tracer served by water and a flow of perfusion indicative of blood flow (i.e., microcirculatory blood flow) in the tissue, the relationship being obtained based on a model that uses at least two compartments placed inside and outside of a flow of blood that diffuses into the tissue of the region to be imaged and that considers temporal changes in the diffusion of the blood flow into the tissue; and a flow quantifying unit configured to quantify the flow of the perfusion in the region to be imaged by applying an amount derived from the image data to the relationship information between the tracer concentration and the flow of the perfusion.

Preferably, the model that uses two compartments placed inside and outside of the flow of blood that diffuses into the tissue of the region to be imaged.

Still preferably, the storing unit comprises means configured to obtain a plurality of amounts of the tracer existing within a unit voxel that corresponds to each of a plurality of known flows by applying to the model representative parameters of the tissue in the region to be imaged; means configured to approximating a relationship between the plurality of known flows and the plurality of amounts of the tracer to either a linear expression or a non-linear expression; and means configured to memorize, as the correspondence information, a correspondence relationship based on either the linear expression or the non-linear expression in the form of either a table or a conversion expression.

It is also preferred that the flow quantifying unit comprises means configured to obtain an amount of the tracer within a unit voxel from signal intensities of the image data based on the ASL technique; and means configured to convert the amount of the tracer into the flow of the perfusion using either the table or the conversion expression. For example, the obtaining means is configured to obtain an ASRL (ASL signal to control signal ratio image) from the image data based on the ASL technique and to calculate the amount of the tracer using the ASLR image.

It is also preferred that the storing unit comprises means configured to use reference data to correct the correspondence relationship between the tracer concentration and the flow of the perfusion.

By way of example, the imaging unit is configured to perform the scan based on an ASTAR (modified STAR using Asymmetric Inversion slabs) technique or on a VS-ASL (Velocity Selective Arterial Spin Labeling) technique.

Still another aspect, there is provided a flow quantification apparatus in which a model indicating a diffusion state of a flow of blood (i.e., microcirculatory blood flow) that diffuses into tissue of a region to be imaged of a subject to be examined is used for quantifying a flow of perfusion in the region to be imaged, the apparatus comprising: a storing unit configured to store therein correspondence information between a concentration of tracer served by water and a flow of perfusion indicative of blood flow in the tissue of the region to be imaged, the relationship being obtained based on the model that uses at least two compartments placed inside and outside of the flow of blood that diffuses into the tissue of the region to be imaged and that considers temporal changes in the diffusion of the blood flow into the tissue; and a flow quantifying unit configured to quantify the flow of the perfusion in the region to be imaged by applying an amount derived from image data obtained by imaging means to the correspondence information between the tracer concentration and the flow of the perfusion.

Preferably, the model that uses two compartments placed inside and outside of the flow of blood that diffuses into the tissue of the region to be imaged.

Still another aspect of the present invention, there is provided a flow quantification apparatus in which a model indicating a diffusion state of a flow of blood (i.e., microcirculatory blood flow) that diffuses into tissue of a region to be imaged of a subject to be examined is used for quantifying a flow of perfusion in the region to be imaged, the apparatus comprising: means configured to obtain a plurality of amounts of a tracer existing within a unit voxel that corresponds to each of a plurality of known flows by applying, to the model, representative parameters of the tissue of the region to be imaged; means configured to approximating a relationship between the plurality of known flows and the plurality of amounts of the tracer to a non-linear expression; and means configured to memorize a correspondence relationship based on the non-linear expression in the form of either a table or a conversion expression, the correspondence relationship being applied to quantifying the flow of perfusion in the region to be imaged.

Still another aspect of the present invention, a flow quantification method is provided in which a model indicating a diffusion state of a flow of blood (i.e., microcirculatory blood flow) that diffuses into tissue of a region to be imaged of a subject to be examined is used for quantifying a flow of perfusion in the region to be imaged, comprising the steps of: storing correspondence information between a concentration of tracer served by water and the flow of perfusion indicative of blood flow in the tissue of the region to be imaged, the relationship being obtained based on the model that uses at least two compartments placed inside and outside of the flow of blood that diffuses into the tissue of the region to be imaged and that considers temporal changes in the diffusion of the blood flow into the tissue; and quantifying the flow of the perfusion in the region to be imaged by applying an amount derived from image data of the subject to the correspondence information between the tracer concentration and the flow of the perfusion.

Still another aspect of the present invention, there is provided a flow quantification method in which a model indicating a diffusion state of a flow of blood (i.e., microcirculatory blood flow) that diffuses into tissue of a region to be imaged of a subject to be examined is used for quantifying a flow of perfusion in the region to be imaged, comprising the steps of: obtaining a plurality of amounts of a tracer existing within a unit voxel that corresponds to each of a plurality of known flows by applying, to the model, representative parameters of the tissue of the region to be imaged, the model being a two-compartment model that uses two compartments placed inside and outside of the flow of blood that diffuses into the tissue of the region to be imaged and being set in consideration of temporal changes in the diffusion of the blood flow into the tissue in the region to be imaged; approximating a relationship between the plurality of known flows and the plurality of amounts of the tracer to a non-linear expression; and memorizing a correspondence relationship based on the non-linear expression in the form of either a table or a conversion expression, the correspondence relationship being applied to quantifying the flow of perfusion in the region to be imaged.

Specific configurations and features according to other arrangements of the present invention will be made clear by the embodiments of the present invention described below and the accompanying drawings.

BRIEF DESCRIPTION OF THE DRAWINGS

In the accompanying drawings:

FIGS. 9A and 9B show tables which illustrate results of simulations performed by the present inventor;

FIG. 12 shows a table which illustrates results of experiments performed by the present inventor;

DESCRIPTION OF THE PREFERRED EMBODIMENTS

Figure 1:
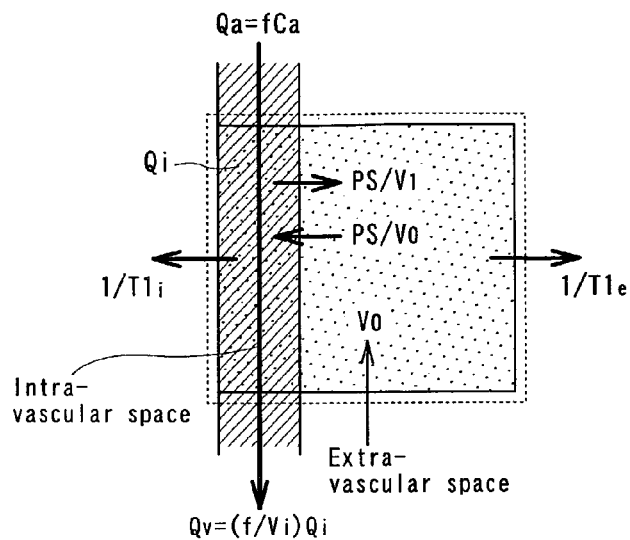
FIG. 1 is an explanatory diagram which illustrates the two-compartment model for describing the principle of the present invention.
Figure 2A:
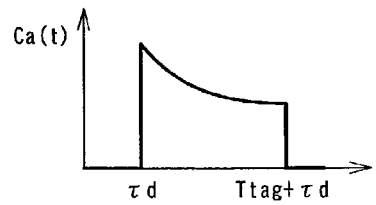
FIGS. 2A and 2B are diagrams which illustrate waveforms of input functions for the PASL technique and the CASL technique, which can be performed in the present invention.
Figure 2B:
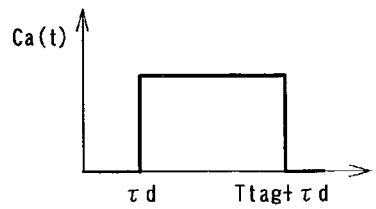
Figure 3A:
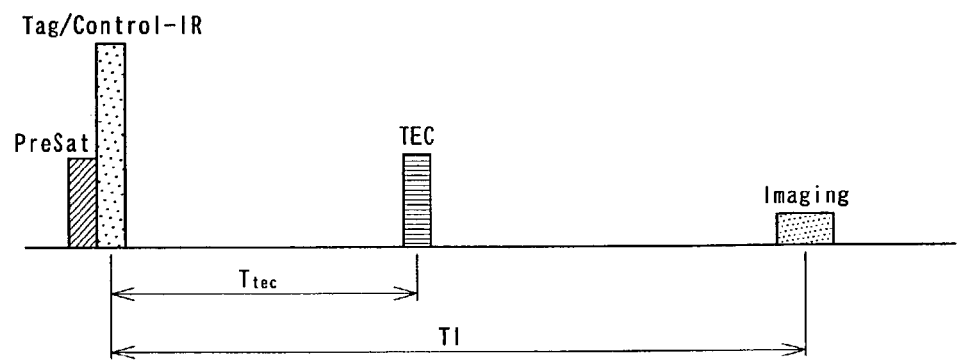
FIGS. 3A and 3B are explanatory diagrams which illustrates a pulse sequence which can be suitably employed in the present invention, and positioning for slabs formed by applied pulses.
Figure 3B:
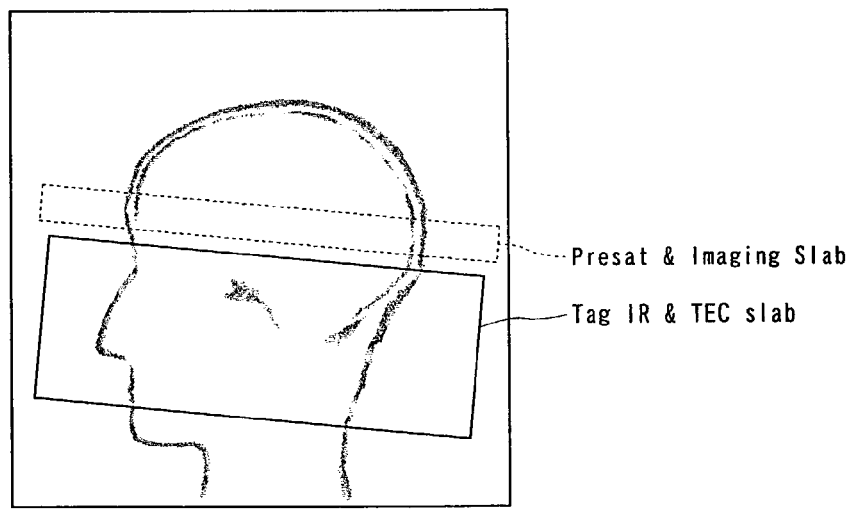
Figure 4A:
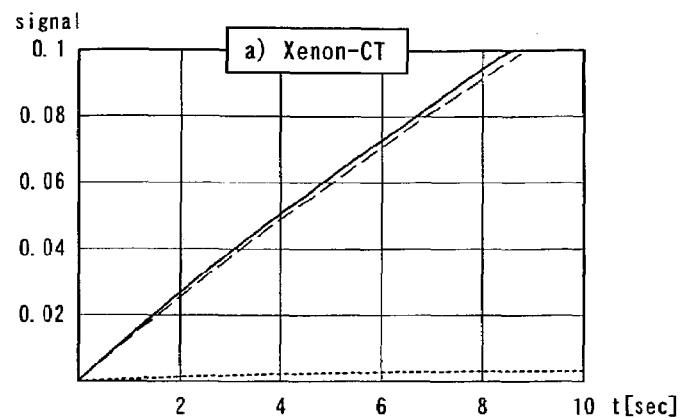
FIGS. 4A through 4D are charts which illustrate results of simulations performed by the present inventor.
Figure 4B:
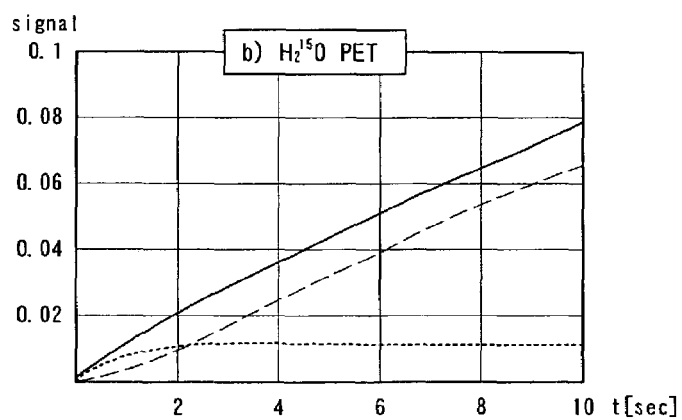
Figure 4C:
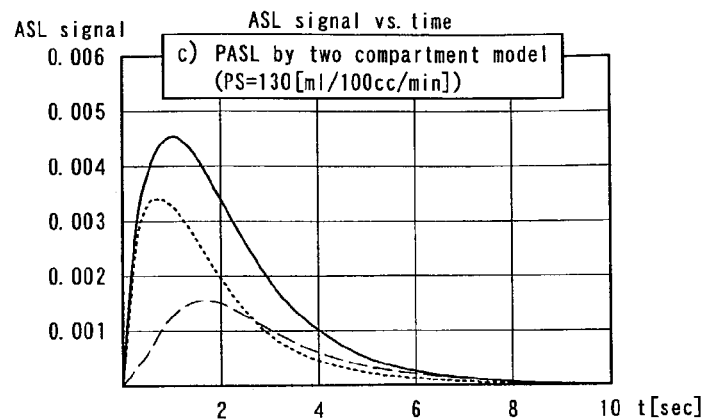
Figure 4D:
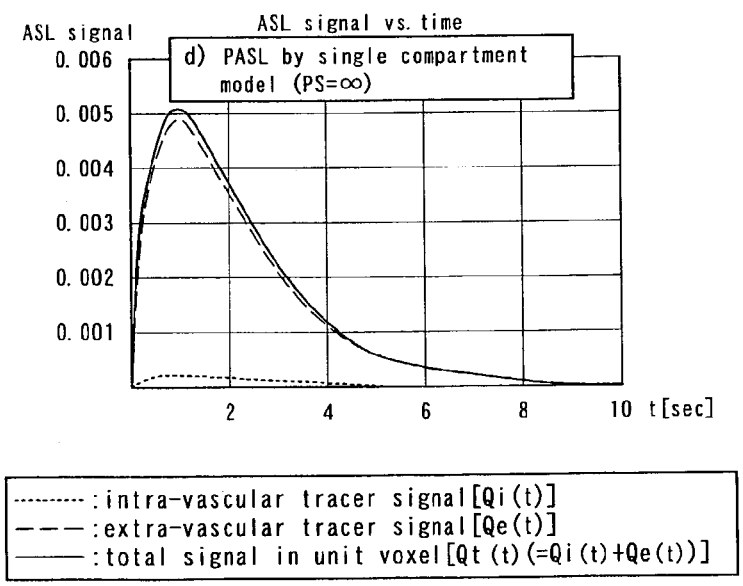
Figure 5:
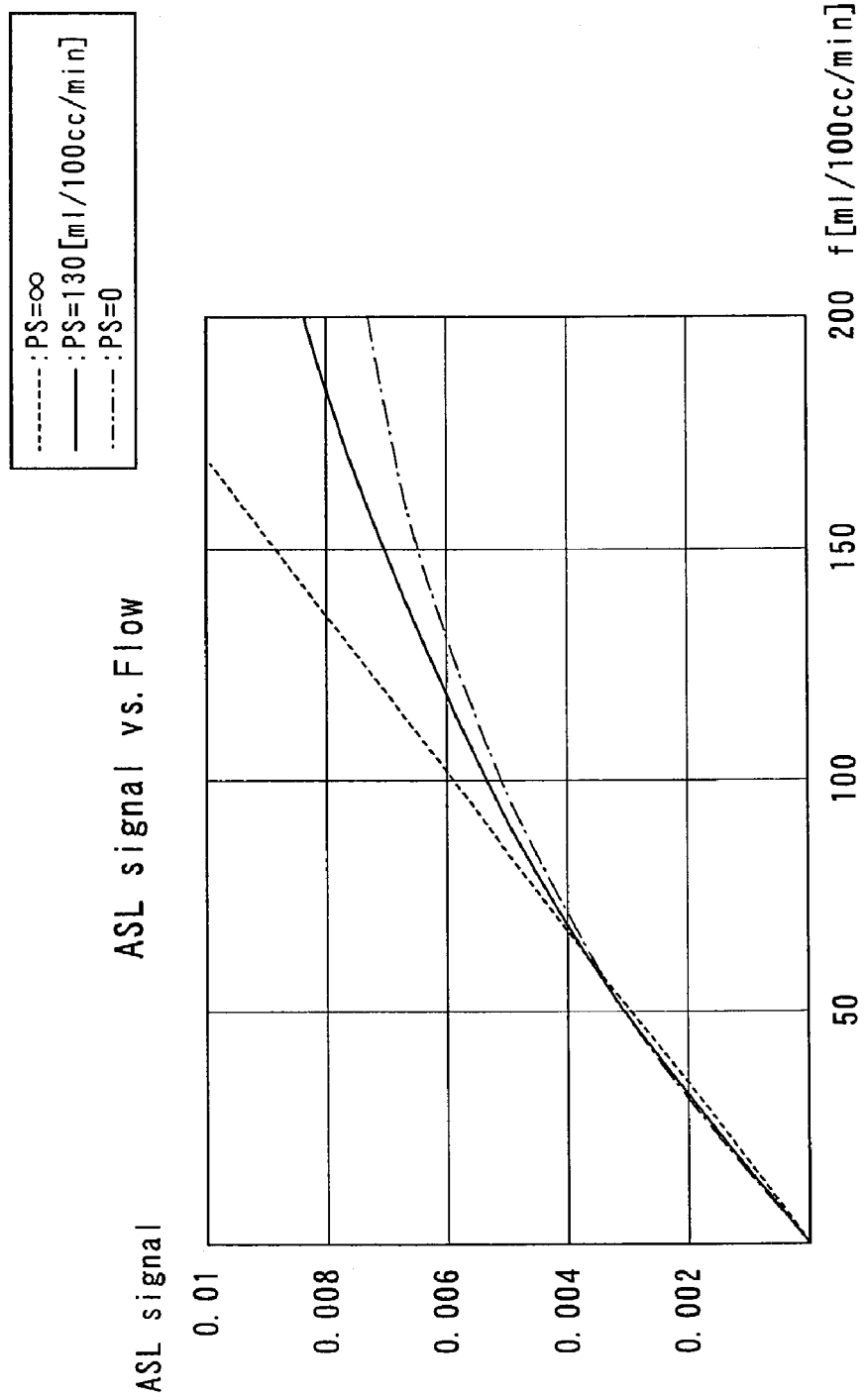
FIG. 5 shows a chart which illustrates results of simulations performed by the present inventor.
Figure 6A:
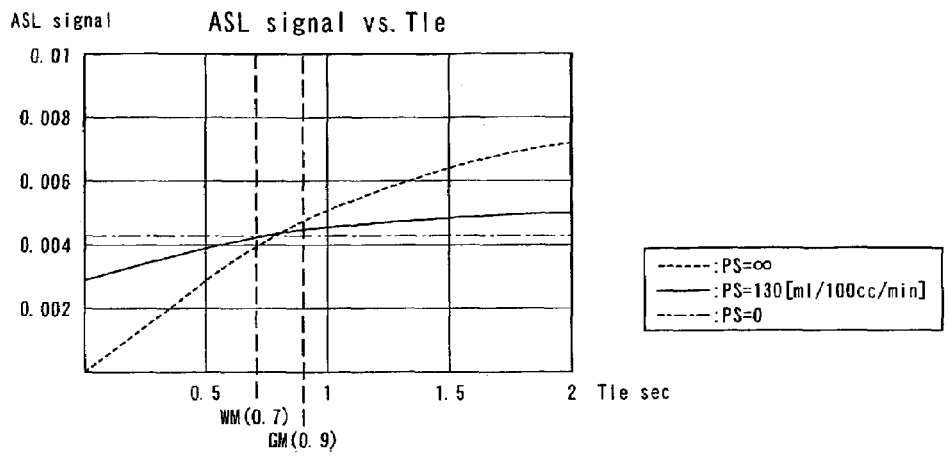
FIGS. 6A through 6C show charts which illustrate results of simulations performed by the present inventor.
Figure 6B:
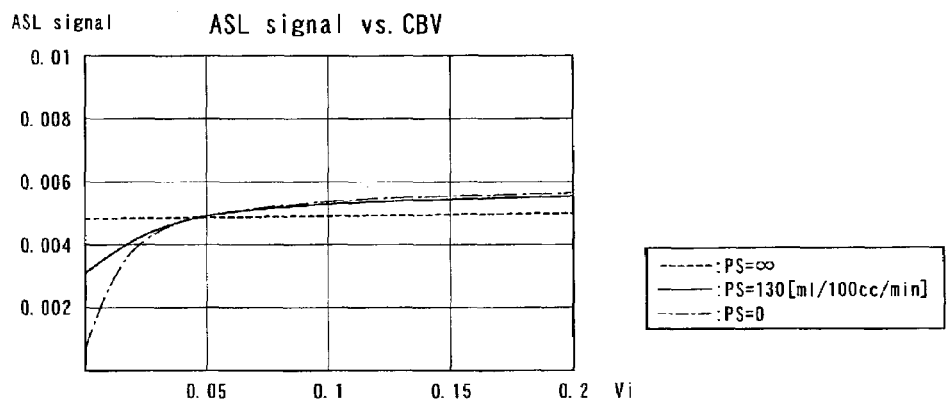
Figure 6C:
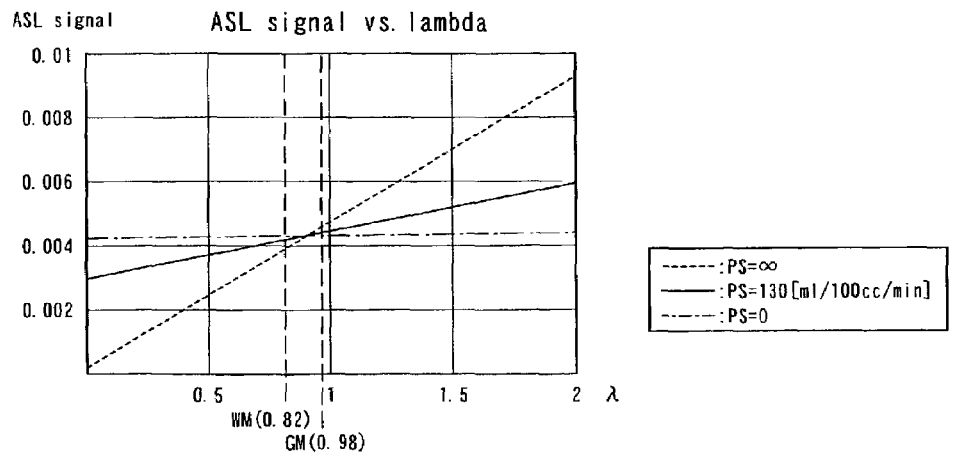
Figure 7A:
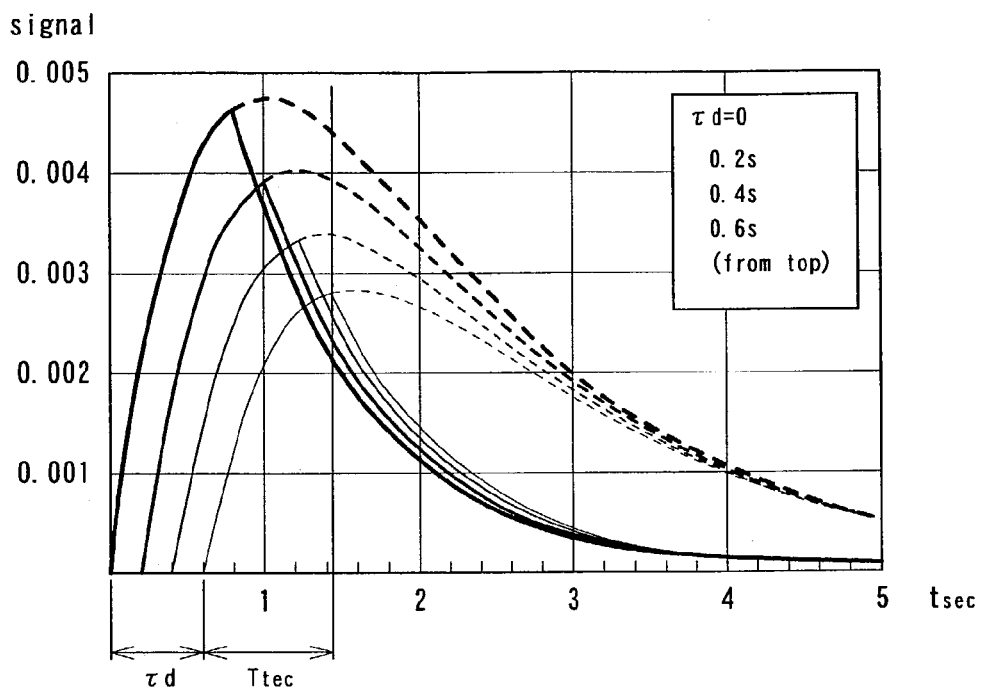
FIGS. 7A and 7B show charts which illustrate results of simulations performed by the present inventor.
Figure 7B:
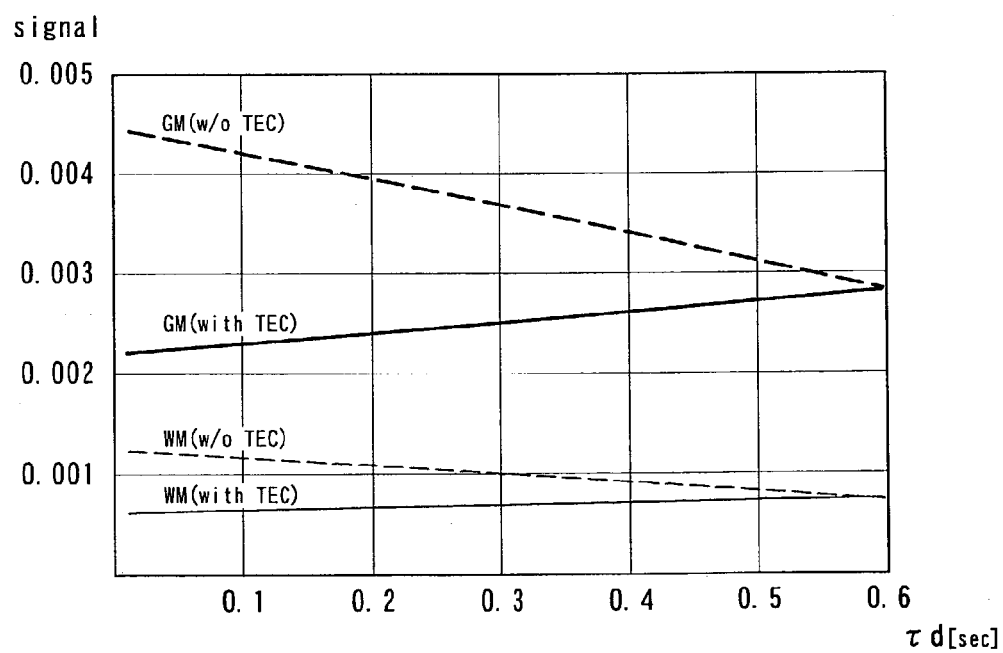
Figure 8:
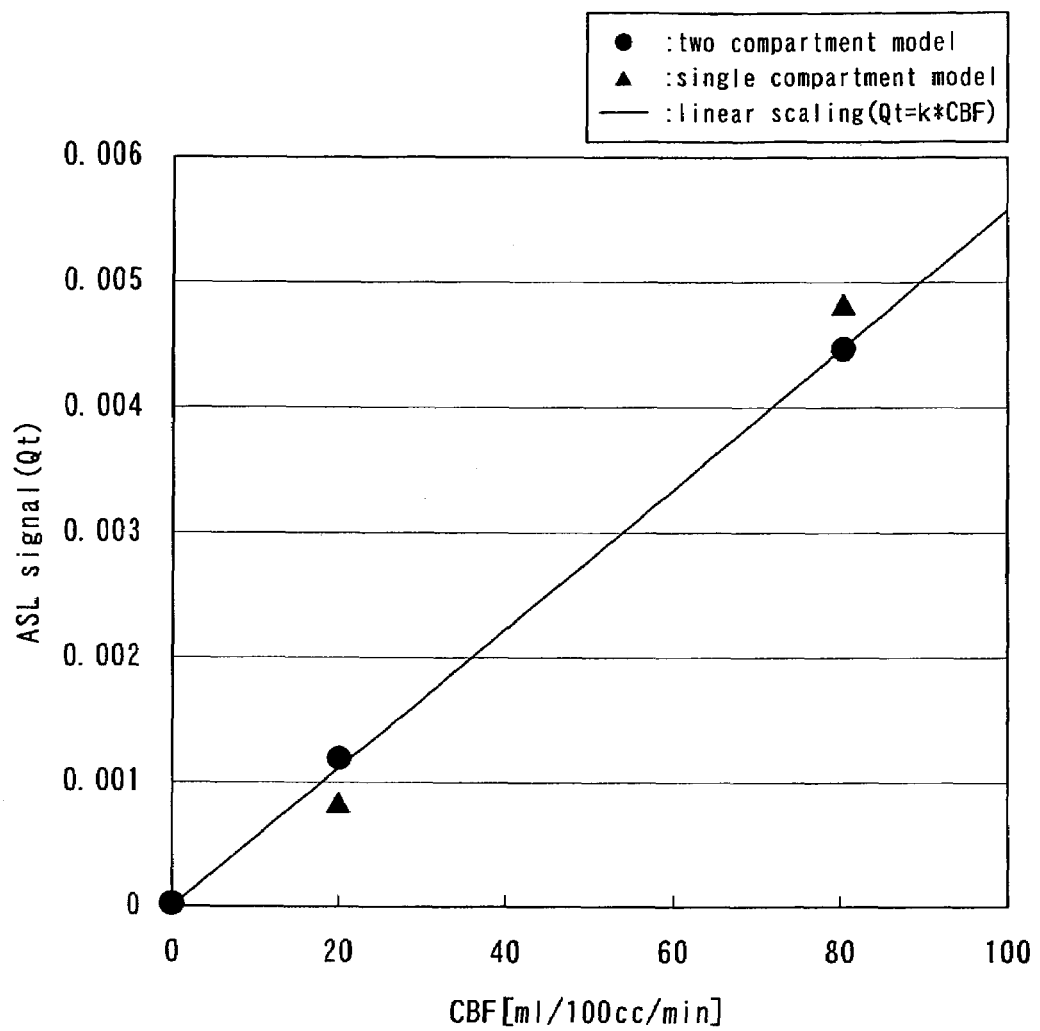
FIG. 8 shows a chart which illustrates results of simulations performed by the present inventor.
Figure 10:
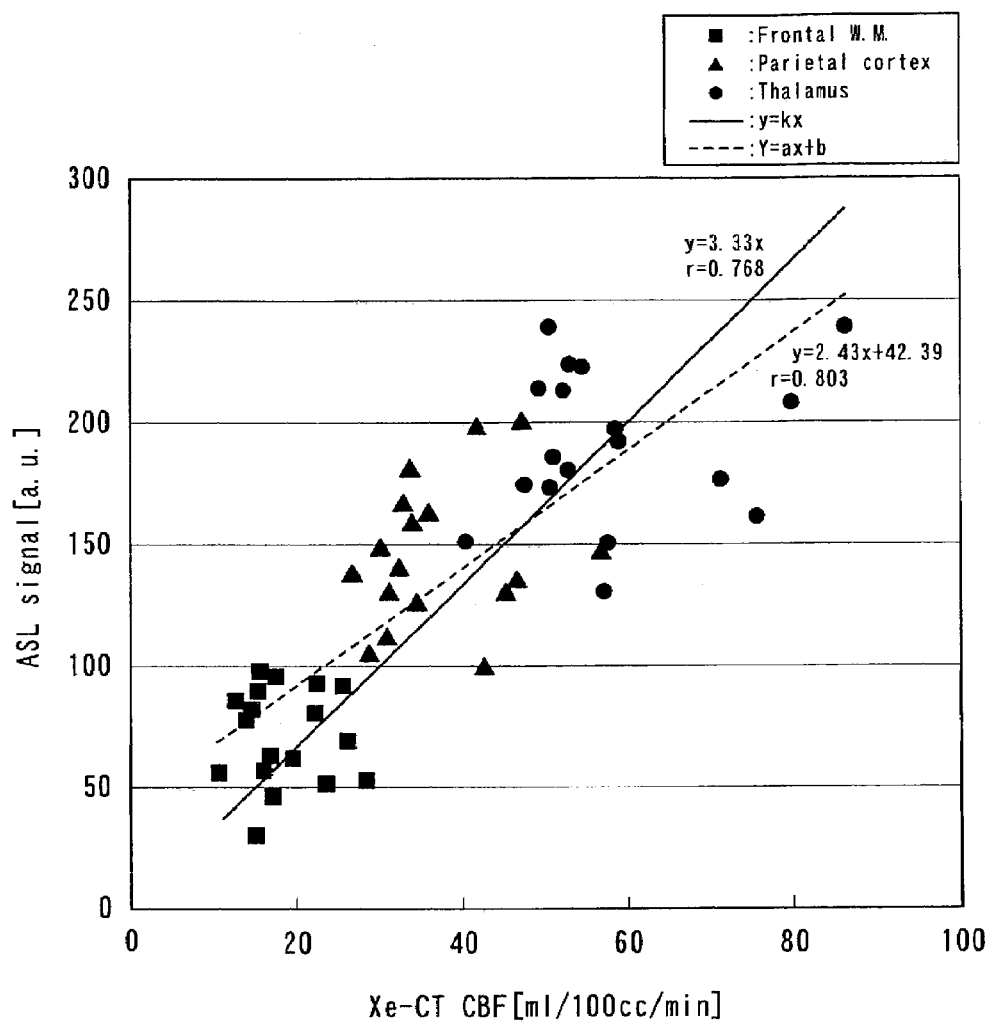
FIG. 10 shows a chart which illustrates results of simulations performed by the present inventor.
Figure 11:
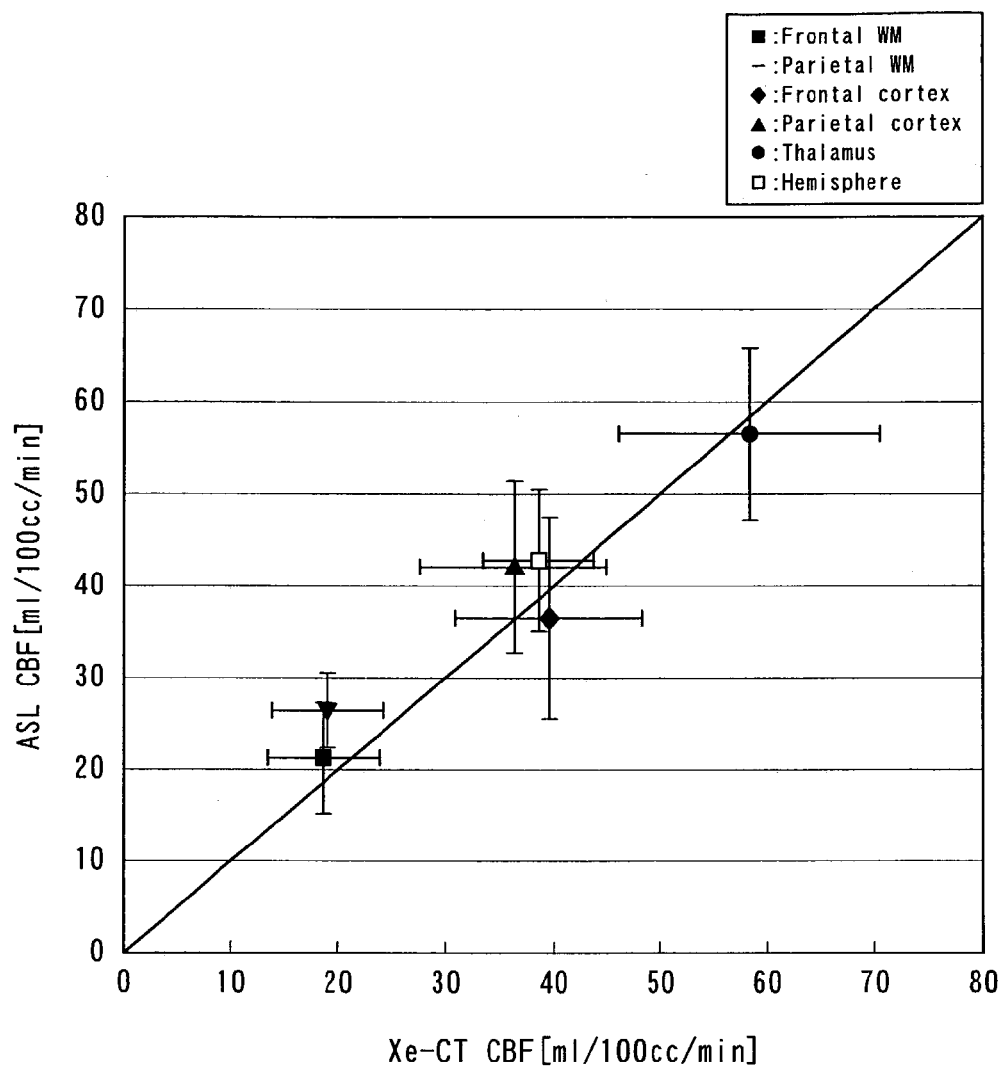
FIG. 11 shows a chart which illustrates results of simulations performed by the present inventor.
Figure 13:
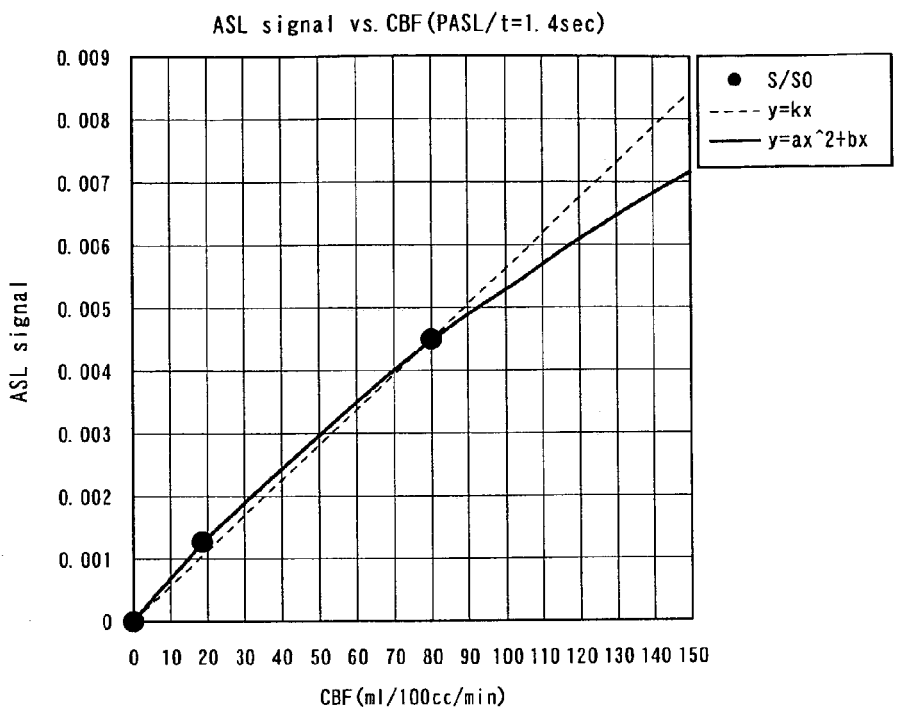
FIG. 13 shows a chart which illustrates results of experiments performed by the present inventor.
Figure 14:
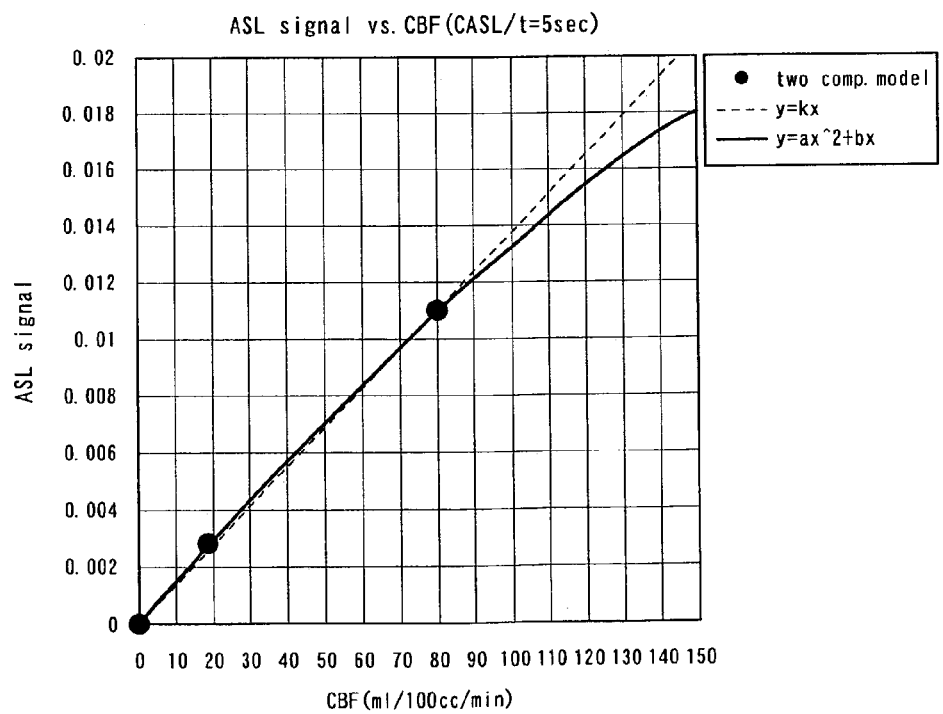
FIG. 14 shows a chart which illustrates results of experiments performed by the present inventor.

Description will be made below regarding an embodiment of the present invention with reference to the accompanying drawings.

Referring to FIGS. 15 through 22, description will be made regarding an MRI apparatus according to an embodiment of the present invention.

The MRI apparatus according to the present embodiment also serves as a flow quantification apparatus with the ASL imaging according to the present invention, and an example wherein the functions of ASL imaging and flow quantification using the results of imaging are integrally provided is shown. Another arrangement may be made wherein a dedicated flow quantification apparatus having a function of flow quantification performs flow quantification according to the present invention.

The MRI apparatus which also serves as a flow quantification apparatus according to the present invention is characterized by performing conversion from the tracer concentration $Q_t$ into the flow f using a memory table stored beforehand.

First of all, description will be made regarding a schematic configuration of the MRI apparatus.

The MRI apparatus comprises, when roughly sectioned, a bed unit for mounting a subject P, a static magnetic field generating unit for generating a static magnetic field, a gradient generating unit for adding positional information to the static magnetic field, a transmission/reception unit for transmitting and receiving high-frequency signals, and a control/calculation unit for performing control of the overall system and reconstruction of images.

The static magnetic generating unit includes a superconducting magnet 1 and a static power supply 2 for supplying current to the magnet 1, for example, and generates a static magnetic field $H_0$ in the axis direction (Z direction) of an opening (a space for diagnosis) having a cylindrical shape, into which the subject P is inserted. Note that a shim coil 14 is provided to the magnet unit. Current is supplied to the shim coil 14 from a shim coil power supply 15 for making the static magnetic field uniform under control of a controller as described later. The top plate of the bed unit wherein the subject P has been mounted into the opening of the magnet 1 can be retractably inserted into the opening.

The gradient generating unit includes a gradient coil unit 3 mounted in the magnet 1. The gradient coil unit 3 includes three sets (types) of x, y and z coils 3x, 3y, and 3z, for generating gradient in the X, Y and Z axis directions, orthogonal one to another. The gradient unit further includes a gradient power supply 4 for supplying a current to the x, y and z coils. The gradient power supply 4 supplies pulse current to the x, y and z coils 3x, 3y, and 3z, for generating gradient under the control of a sequencer 5 as described later.

The pulse current supplied from the gradient power supply 4 to the x, y, z coils 3x, 3y, and 3z, are controlled so as to synthesize gradients in the X, Y, Z directions, which are three physical axes, whereby each of the slice direction gradient Gs, the phase encoding direction gradient Ge, the readout direction (frequency encode direction) gradient Gr, which are theoretical axes, can be arbitrary set and altered. Each of gradients in the slice direction, phase encoding direction, and readout direction, are superimposed on the static magnetic field $H_0$.

The transmission/reception unit includes an RF coil 7 disposed near the subject P in the imaging space within the magnet 1, a transmitter 8T, and a receiver 8R, connected to the coil 7. The transmitter 8T and the receiver 8R supply RF current pulses of the Larmor frequency to the RF coil 7 for an effecting magnetic resonance (MR) phenomenon, and also receive high-frequency MR signals received by the RF coil 7, and perform various types of signal processing for the received signals, under control of the sequencer 5 as described later, whereby corresponding digital signals can be formed.

Furthermore, the control/calculation unit includes a sequencer 5 (which is also referred to as sequence controller), a host computer 6, a calculator 10, a storage 11, a display device 12, and input device 13. Of these, the host computer 6 has functions of receiving information which an operator has specified, according to the stored software procedures, commanding the scan-sequence information based upon the received information to the sequencer 5, and also control the operation of the overall apparatus including the calculator 10, the storage 11, and display device 12, not to mention the sequencer 5.

The sequencer 5 includes a CPU and memory, and stores the pulse-sequence information which has been transmitted from the host computer 6, and controls a series of operations of the gradient power supply 4, transmitter 8T, and the receiver 8R, according to the information. Furthermore, the sequencer 5 temporarily stored digital data of MR signals from the receiver 8R, and transmits the data to the calculator 10 for performing reconstruction processing.

Now, the pulse-sequence information indicates the entire information required for operating the gradient power supply 4, the transmitter 8T, and the receiver 8R, according to a series of pulse sequences, and including the information with regard to the intensity of the pulse current applied to the x, y, z coils 3x, 3y, and 3z, the duration time for applying the pulse current, and the timing for applying the pulse current.

Optional techniques can be employed as the ASL imaging technique of the present embodiment, such as the ASTAR technique, the STAR (signal targeting with alternating radio frequency) technique, EPISTAR (echo planar MR imaging and signal targeting with alternating radio frequency) technique, FAIR (flow-sensitive alternation inversion recovery) technique, or the like. Also, as a pulse sequence which can be employed in these techniques, any pulse sequence can be employed so long as the pulse sequence is that for high-speed imaging, which enhances the quantity of the longitudinal magnetization. For example, the fast FE technique, the fast SE technique, the EPI (Echo Planer Imaging) technique, the FASE (fast asymmetric SE) technique, the hybrid EPI technique, or the like, can be employed.

The calculator 10 performs readout input raw data, positioning of the raw data to the Fourier space (which is also referred to as k space or frequency space) of an image, averaging processing for the data, differential processing for data between the tag mode and the control mode, threshold processing for data, processing for forming absolute values from complex data, reconstruction processing for reconstructing raw data into real spatial data (e.g., two-dimensional, or three-dimensional Fourier conversion) in a suitable sequence. Note that, in order to handle three-dimensional imaging, the calculator 10 is designed so that MIP (maximum value projection) processing can be performed for generating two-dimensional image data from three-dimensional image data.

The storage can not only store raw data and reconstructed image data but also store the image data subjected to calculation processing. The display device 12 displays an image. Also, the surgeon can input the required information such as desired scan conditions, scan sequence, image processing technique, and the like, to the host computer 6 with the input device 13.

Next, operation examples of the present embodiment will be described.

Figure 16:
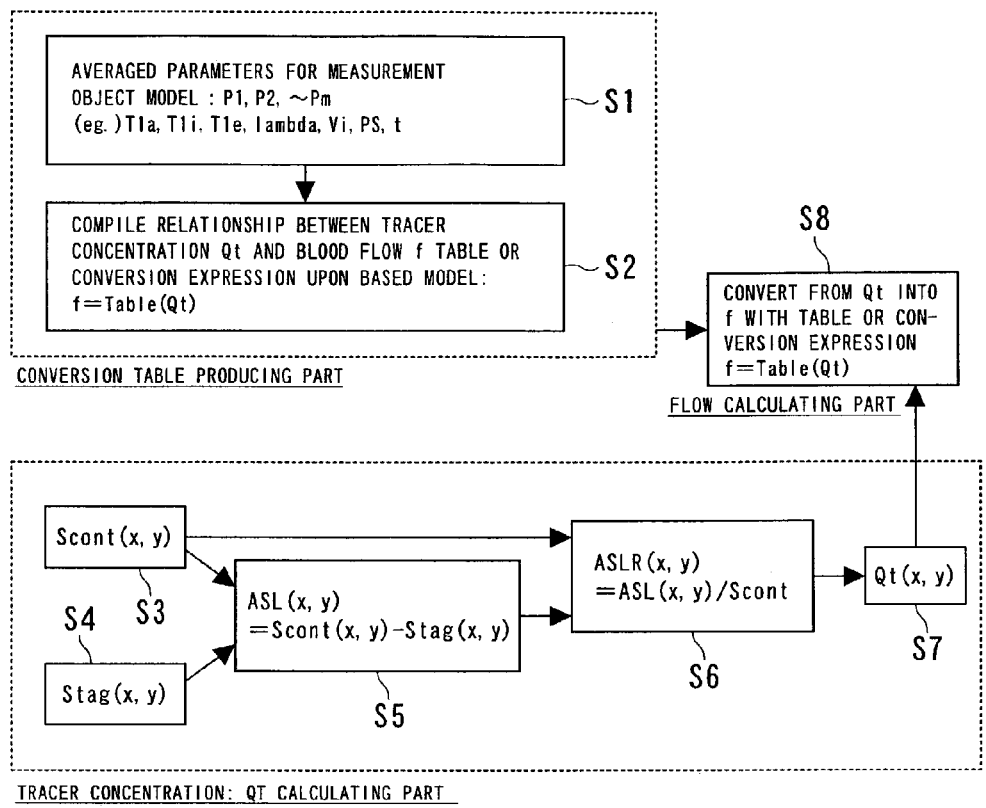
FIG. 16 is a flowchart which illustrates a schematic example of flow quantification by table conversion in ASL imaging according to an embodiment of the present invention.

FIG. 16 illustrates a processing example for flow quantification in the ASL imaging according to the present embodiment. The processing is performed by the host computer 6 or the calculator 10 having functions for flow quantification.

In the case of the processing example, first of all, a conversion equation or a table for converting the tracer amount $Q_t$ into the flow f is formed. That is, the relation between the tracer concentration $Q_d$ and the flow f is represented with a table according to the measuring object model (two-compartment model) based upon average parameters P1, P2, ..., Pm, for the measuring object model (e.g., $T1_a$, $T1_i$, $T1_e$, $\lambda$, $V_i$, PS, t (fixed value), and so forth) (Steps S1 and S2). Thus, the table which determines the relation f=Table($Q_t$) is prepared. With the table, the relation between the flow f and the tracer amount $Q_t$ is determined with linear scaling (i.e., f=K·$Q_t$: K is the proportional coefficient) or a polynomial for approximation. Note that the fixed value t is a value which is directly input from a device such as a user interface.

Detailed description will be made below regarding the aforementioned processing for forming a table.

Let us say that the following relation holds.

$$Q_t = \text{function}(P1, \ldots, Pn, f) \tag{9}$$

wherein $Q_t$ is the tracer amount per unit voxel (tracer concentration), wherein f is the flow, and wherein P1 through Pn are other parameters with regard to the flow, which are generally employed for representing the two-compartment model.

Next, the above relation is reduced to the following expression with regard to k number of dominant parameters having influence on $Q_t$.

$$Q_t = \text{function}(P1, \ldots, Pk, f) \quad k \leq n \tag{10}$$

In the event that k is 0, Expression (9) is reduced to the following expression depending upon only the flow.

$$Q_t = \text{function}(f)$$

Next, a table (or conversion equation) representing the relation between $Q_t$ and f is compiled according to the following procedure. The formation is performed at a suitable timing prior to flow quantification using the calculating function of the host computer 6 or the calculator 10 between the operator and the apparatus side in a interactive manner.

1): In the first step, the flow f is obtained by performing simulation according to the two-compartment model based upon the parameters for representative tissue portions so as to obtain the tracer amount $Q_t$.

With the flow f as f1, f2, and so on through fk, the tracer amount $Q_t(f1)$, $Q_t(f2)$, and so on through $Q_t(fk)$ can be obtained. Note that the tracer amount $Q_t(f1)$, $Q_t(f2)$, and so on through $Q_t(fk)$ may obtained from experimental data, rather than from simulation.

2): In the next step, approximation is performed for the relation between $Q_t$ and f using a linear equation or a higher-order equation. In the event of using a polynomial as a higher-order equation, approximation for the polynomial passing through the origin, $Q_t(f1)$, $Q_t(f2)$ . . . , is made with the following expression.

$$Q_t = a1 \cdot f^m + a2 \cdot f^{(m-1)} + \ldots + am \cdot f \tag{11}$$

Figure 17A:
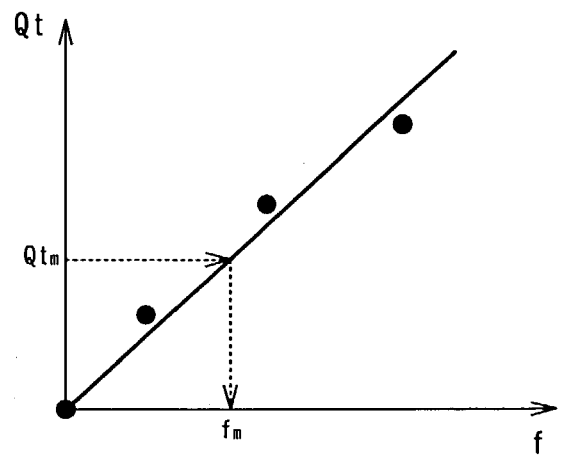
FIGS. 17A and 17B show schematic diagrams which describe calculation of flow using the linear-scaling and the scaling based upon polynomial approximation.
Figure 17B:
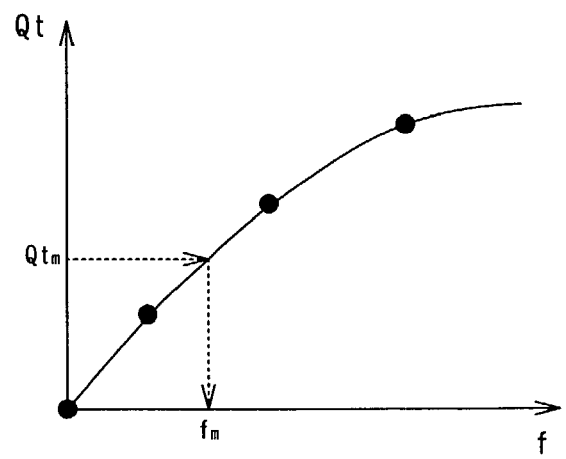

Accordingly, in the event of m being 1, approximation is made with a straight line passing through the origin and one point (linear scaling) as shown in FIG. 17A. In the event of m being 2, approximation is made with a curve passing through the origin and two points (quadric curve approximation), and furthermore, in the event of m=k, approximation is made with a curve passing through the origin and k number of points as shown in FIG. 17B.

Figures 18, 19:
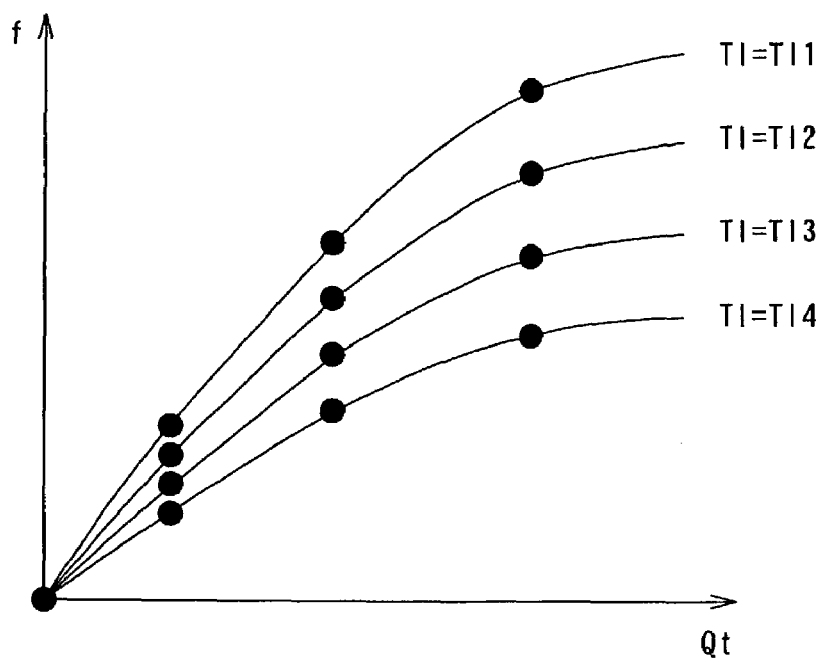
FIG. 18 is a diagram which describes a memory table for flow quantification.
FIG. 19 is a chart which illustrates curve examples for polynomial approximation, taking the duration T1 from the application of tag pulses up to imaging as a parameter.

3): In the next step, a table is compiled from the relation between $Q_t$ between f with re-sampling. Specifically, a discrete table is formed with re-sampling as shown in FIG. 18. In this case, the table is formed for each of parameters P1 through Pk.

Also, the table may be compiled by solving the following expression based upon the two-compartment model with regard to the flow f in an analytical manner.

$$f = \text{function}(P1, P2, \ldots, Pm, Q_t) \tag{12}$$

In this case, the solution is a continuous function, and in the event that the expression cannot be solved in an analytical manner, the expression may be solved in a numerical manner. Furthermore, in the event that the expression cannot be solved both in an analytical manner and a numerical manner, the above-described technique using re-sampling is preferably employed.

Note that an arrangement may be made wherein a conversion equation is stored instead of a table. In this case, a linear equation representing a straight line or a high-order equation representing a curve, which has been obtained for approximation in the above-described Step 2), is stored, and the conversion expression is used for each flow quantification.

Note that, in the event that parameters P1, P2, and so on through Pm other than the flow f are required for calculating the tracer amount $Q_t$, there is need to compile the table for the relation between $Q_t$ and f for each of the parameters P1 through Pm. Also, in the event that the flow depends upon the parameters P1, P2, and so on through Pk, in tissue, tables wherein flow corresponding to each parameter is used are compiled. While a discrete table is required, in the event that the table is obtained with a function, continuous values are obtained.

FIG. 19 illustrates a brain example with the time period TI following application of tag pulses as only one valid parameter (k=1) (P1=TI). For example, in a case of WM and GM in the brain, two points are formed with combination of individual parameters (m=2), and fitting is made for these points including the origin with a linear equation or a quadratic equation. The straight line or the quadratic curve, obtained in fitting processing, is sampled so as to compile a table.

As described above, prior to the ASL imaging, discrete tables representing the relation between $Q_t$ and $f$ are compiled in one way or another. The tables are stored in memory of the storage 11, for example, and are used in quantification processing performed by the calculator 10 or the host computer 6.

Next, the ASL imaging is preferably performed with the ASTAR technique according to the command from the operator. The operating command is executed by transmitting control information based upon pulse-sequence for the ASTAR technique from the sequencer 5 to the gradient power supply 4, the receiver 8R, and the transmitter 8T. The ASTAR technique can be performed with the PASL technique or CASL technique.

A brief description will now be made regarding the ASTAR technique with reference to FIG. 20.

Figure 20:
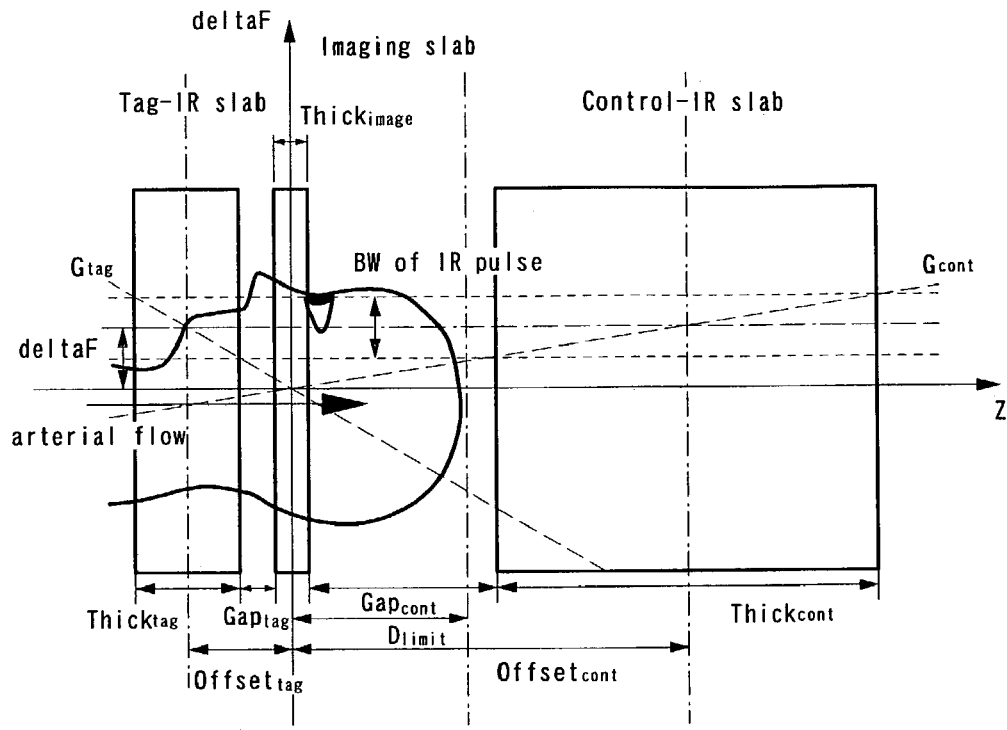
FIG. 20 is a diagram for making further detailed description regarding the ASTAR technique in the ASL imaging according to an embodiment of the present invention.

FIG. 20 illustrates the positioning of slabs spatially placed with the ASTAR technique based upon the PASL technique. In the drawing, let us say that the body axis direction Z of the subject is taken as the horizontal axis, and modulation frequency offset quantity from the center of the imaging slab in the Z axis direction is taken as the vertical axis. Two broken lines drawn at a slant indicate IR (inversion recovery) gradient intensity.

With the ASTAR technique (based upon the PASL technique), as shown in FIG. 20, a tag slab (Tagging slab, or Tag-IR slab) formed by application of tag-IR (inversion) pulse, and a control slab (Controlling slag or Control-IR slab) formed by application of control-IR pulses, are selectively set as to an imaging slab which is selectively set as an imaging area.

Subsequently, a scan using a first pulse sequence (tag (label) scan) made up of a pulse train including tag-IR pulses for being selectively applied to the tag slab and a imaging pulse train for being selectively applied to the imaging slab, and a scan using a second pulse sequence (control scan) made up of a pulse train including control IR pulses for being selectively applied to the control slab and an imaging pulse train for being selectively applied to the imaging slab, are performed over time in an appropriate order. The imaging mode for performing tag scan will be referred to as tag mode, and the imaging mode for performing control scan will be referred to as control mode.

In the event of performing tag scan and control scan, the thickness and the position offset of the slab formed by each imaging pulse is altered with the same ratio under the condition that the offset frequencies for the tag IR pulses and the control IR pulses from the center of the imaging slab are set to the same value. The positioning technique is one of the features of the ASTAR technique used in the present embodiment. Thus, the distance between the tag slab and the control slab, and the imaging slab, can be adjusted, while the MT effect occurring accompanied by application of both IR pulses becomes the same or approximately the same, and imaging can be performed for only the blood flow from one direction.

In the event of imaging the head of the subject, for example, with the ASTAR technique, the tag IR slab is set on the lower-limb side (downstream) from the imaging slab due to artery flowing from the lower-limb side to the apex side, and on the other hand, the control IR slab is set on the apex side (upstream) from the imaging slab. With the ASTAR technique, it is necessary that the control IR slab is set so as not to overlap with the apex including veins. That is to say, the control IR slab is set at a position away from the apex.

With the ASL technique, it is preferable that the signals detected from the vein system are excluded. That is to say, in practice, the imaging slab should not contain the signals from veins for inversion (TI) time. Due to the vein flowing at relatively low speed as compared with the artery flowing, there is no need to apply the tag IR pulses for setting the tag IR slab at a position completely away from the head, but rather, the tag IR slab can be set at a position offset from the imaging slab by a suitable margin according to conditions such as the vein flow speed, the distance between the gap, inversion time, and the like.

Figure 21:
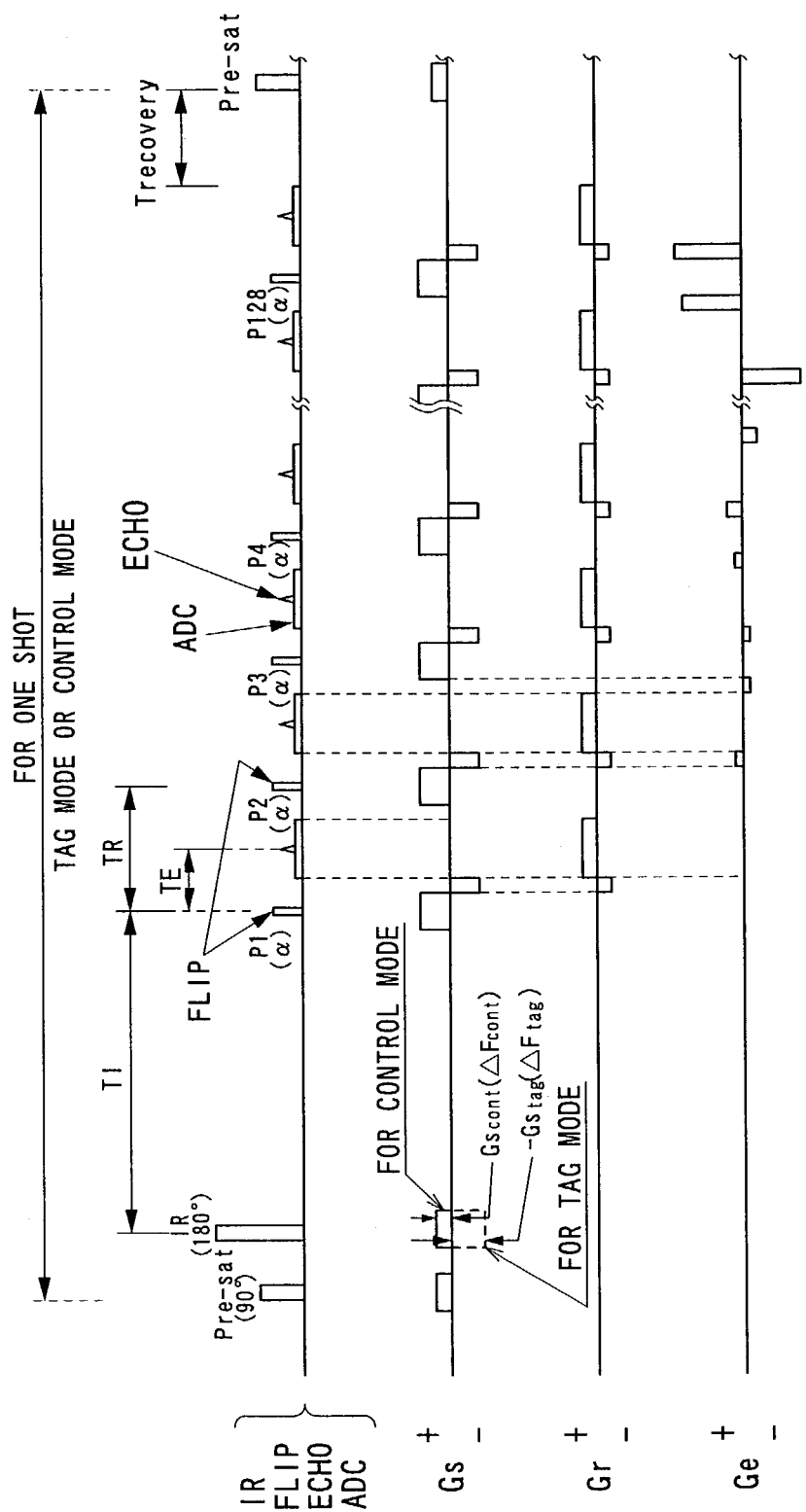
FIG. 21 is a diagram which illustrates a pulse sequence examples according to the ASTAR sequence.

FIG. 21 illustrates a detailed example of a pulse sequence for performing the above-described ASTAR technique (based upon the PASL technique). The pulse sequence example is made up of a pulse train based upon a sequence for the fast FE technique using the IR pulses.

The above-described ASTAR technique is performed, and then, using echo data obtained with the control mode and the scan mode, the control image $S_{cont}(x,y)$ and the tag image $S_{tag}(x,y)$ are reconstructed by the calculator 10 for the desired portion such as the head (Steps S3 and S4).

Subsequently, differential processing is performed for the reconstructed control image $S_{cont}(x,y)$ and tag image $S_{tag}(x,y)$ by the calculator 10 as represented with the following Expression (13), whereby the ASL image ASL(x,y) is formed (Step 5).

$$ASL(x,y)=S_{cont}(x,y)-S_{tag}(x,y) \tag{13}$$

Subsequently, the ratio of the ASL image ASL(x,y), which has been measured in practice as to the control image value $S_{cont}$ is obtained for each pixel by the calculator 10 based upon the following Expression (14), whereby a normalized ASLR (ASL signal to control signal ratio) image ASLR(x,y) is obtained (Step S6).

$$ASLR(x,y)=ASL(x,y)/S_{cont} \tag{14}$$

Note that $S_{cont}$ denotes image value of WM or blood on the control image. In the event that the recovery time $T_{rep}$ is too short to regard the image value as reflecting the proton density (i.e., the recovery time $T_{rep}$ is shorter than 2 sec), the $S_{cont}$ is employed from another image which has been taken with a suitably long recovery time $T_{rep}$.

Here, description will be made below regarding the reason that the image value $S_{cont}$ is employed. With the parameter depending upon the apparatus such as a transmission/reception gain, and the like, as G, and with the coefficient depending upon the labeling technique (e.g., inversion angle, and so forth), T2 relaxation, and the like, as A, the tracer signal intensity (ASL) is represented by the following Expression (15).

$$\text{Tracer signal intensity ASL signal}=G \cdot A \cdot Q_t \cdot M_0 \tag{15}$$

Reckoning the image value $S_{cont}$ to be being measured over a long duration TI sufficient for T1 relaxation to be saturated, the following Expression (16) holds.

$$S_{cont}=G \cdot A \cdot M_0 \tag{16}$$

Accordingly, the following Expression (17) holds.

$$ASLR = (G \cdot A \cdot Q_t \cdot M_0)/(G \cdot A \cdot M_0) = Q_t \quad (17)$$

Thus, the influence of G, A, and $M_0$, is cancelled, and the conversion can be made simply by referring to the table.

For example, let us consider the brain. In order to obtain the image value $S_{cont}$, there is the need to measure $M_0$ for blood, however, measurement of $M_0$ for blood is difficult, so the signal intensity obtained from white matter may be used as a substitute for blood.

On the other hand, in the event of a single slice, the image value $S_{cont}$ should be obtained at one position for each subject, and in the event of multiple slices, the image value $S_{cont}$ should be obtained for each slice for each subject due to the efficiency of the coil not being uniform spatially.

Figure 15:
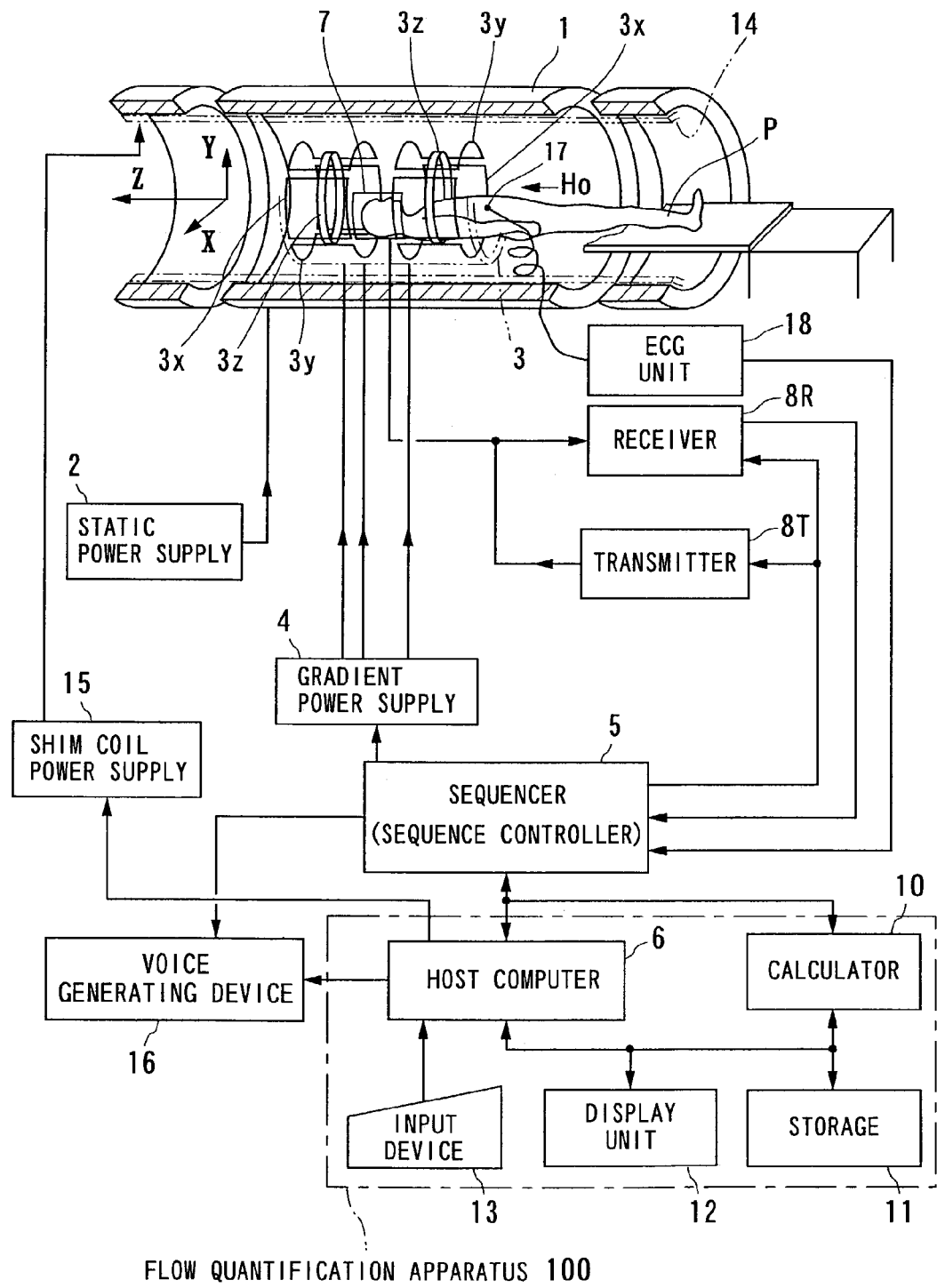
FIG. 15 is a block diagram which illustrates an example of an MRI apparatus according to an embodiment of the present invention.

Note that, with the configuration of above-described embodiment, the host computer 6, the calculator 10, the storage 11, the display device 12, and the input device 13, of the MRI apparatus, are components serving as components of the flow quantification apparatus 100 according to the present invention, as well (refer to FIG. 15).

First of Other Embodiments

While, with the above-described embodiment, an arrangement is made wherein a table indicating the relation between the tracer flow amount $Q_t$ and the flow f is obtained one way or another at a certain point in time, an arrangement may be made as another embodiment wherein the flow f is directly converted from the tracer flow amount $Q_t$ based upon the functional relation between the flow f and the tracer flow amount $Q_t$.

Specifically, with the relation between the $Q_t$ and f, which was obtained in the simulations based upon the two-compartment model and the representative tissue parameters in the above description of flow quantification using a table, the vertical axis and the horizontal axis are interchanged so as to being transformed into the above-described Expression (12) with the flow f as the vertical axis. That is, the relation between the $Q_t$ and f should be subjected to fitting with the following curve (polynomial) for the flow f, passing through $f(Q_{t1})$, $f(Q_{t2})$, and so forth.

$$f = b1 \cdot Q_t^m + b2 \cdot Q_t^{(m-1)} + \ldots + bm \cdot Q_t \quad (18)$$

As described above, in the event of employing the direct conversion technique, there is no need to solve Expression (11) with regard to f.

Figure 22A:
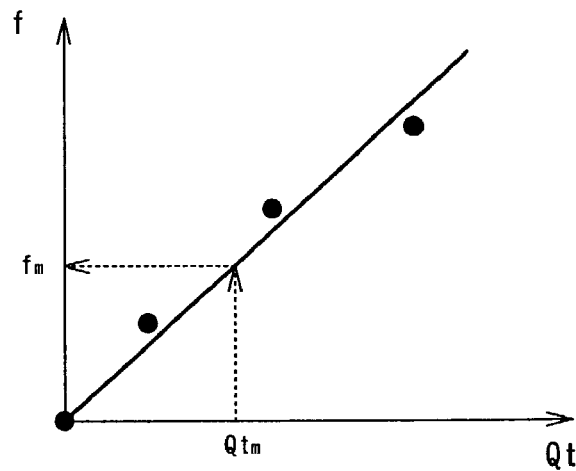
FIGS. 22A and 22B show schematic diagrams for describing flow calculation using scaling based upon linear-scaling and scaling with polynomial approximation.
Figure 22B:
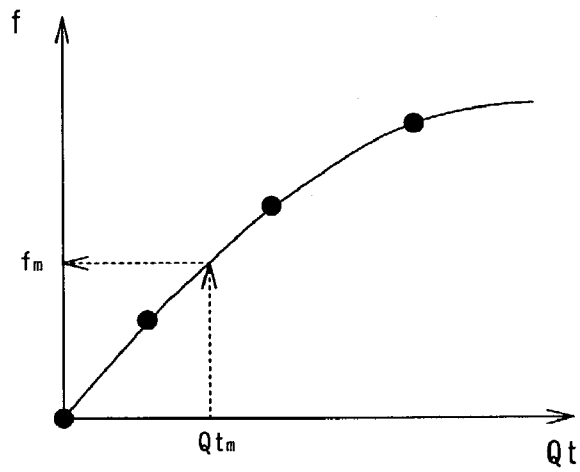

FIGS. 22A and 22B show procedural examples wherein fitting is performed for the relation between $Q_t$ and f with the vertical axis and the horizontal axis interchanged, and the flow f is obtained from the tracer flow amount $Q_t$ as described above. FIG. 22A illustrates flow quantification with linear approximation (linear scaling), corresponding to FIG. 17A described above. On the other hand, FIG. 22B illustrates flow quantification with polynomial approximation, corresponding to FIG. 17B described above.

Using the thus-approximated straight line or the curve, a discrete table is compiled by performing re-sampling (see FIG. 18). For example, a table for the flow f is formed at intervals of 1 [ml/100 cc/min]. Also, the table may be formed for each of parameters P1 through Pk.

Note that an arrangement may be made wherein a conversion expression is stored instead of a table. In this case, a linear equation representing a straight line or a curve representing a higher-order equation, formed for approximation, is stored as the conversion expression, and the conversion expression is called up for each flow quantification.

Note that in the event that the parameters P1, P2, and so forth through Pm, other than the flow f, are required for calculating the tracer amount $Q_t$, there is the need to compile the table for the relation between $Q_t$ and f for each of parameters P1 through Pm. Furthermore, in the event that flow depends on the parameters P1, P2, and so forth through Pk, in tissue, tables wherein flow corresponding to each parameter is used are compiled. While a discrete table is required, in the event that the table is obtained with a function, continuous values are obtained.

Second of Other Embodiments

With the above-described embodiment, in particular, the influence of the difference in the reception gain may be corrected using reference data. A correction example will be described below.

Figure 23:
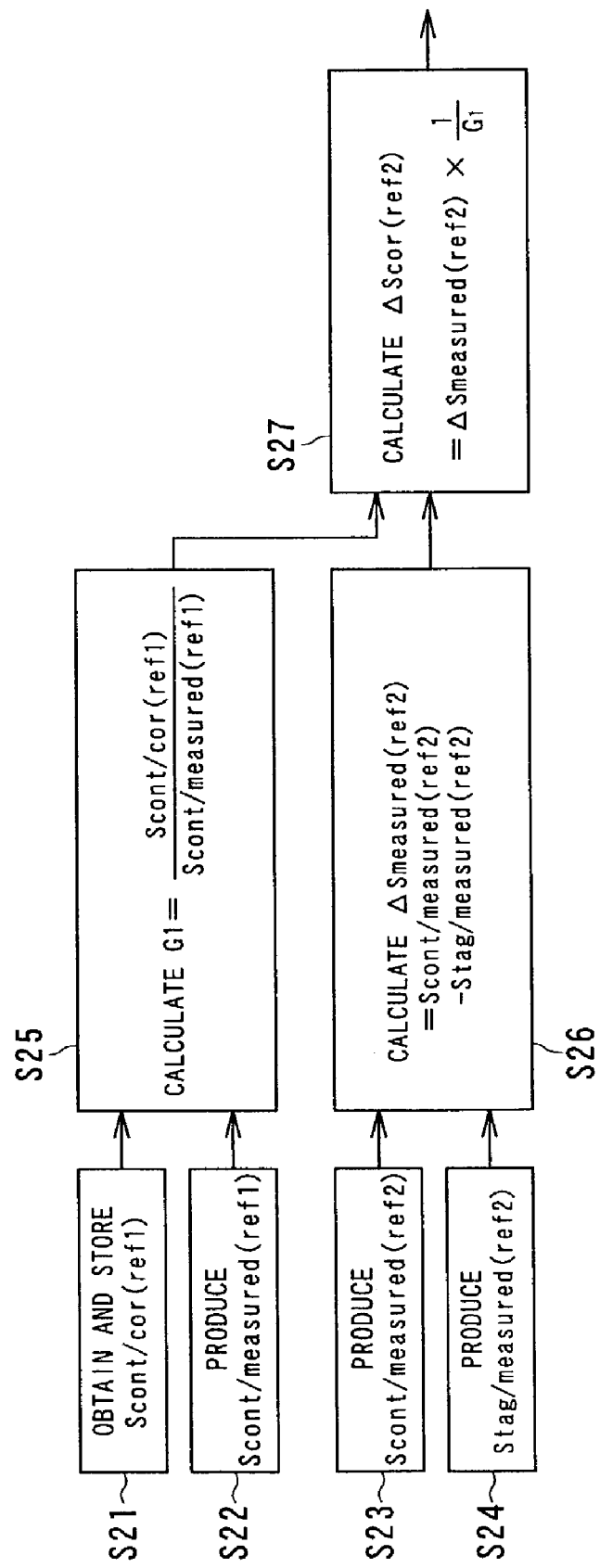
FIG. 23 is a flowchart for describing correction of scaling using reference data according to another embodiment of the present invention.

The corrected image value $S_{cont/cor}(\text{ref1})$ for a static reference phantom ref1 (see FIG. 23) is subjected to statistical calculation processing with the reception gain for the control mode beforehand, and is stored in the storage 11 (Step S21 in FIG. 23). The reference phantom ref1 is a phantom with T1 close to blood (with the static magnetic field of 1.5 T, T1 is 1200 msec to 1500 msec). While the calculation can be performed by the calculator 10 or the host computer 6, an arrangement may be made wherein another external device other than the present MRI apparatus performs the calculation processing, the computed data is transmitted to the host computer 6 through the input device 13, and is stored in the storage 11.

Note that tissue of the head itself can be used for calculating the reception gain $G_1$ for substituting for the static reference phantom ref1.

Subsequently, the ASL imaging, i.e., the control scan and the tag scan, is performed one time for each of the subject and the static reference phantom ref1 in a suitable order under the condition that the static reference phantom ref1 being placed near the head of the subject. The control scan and the tag scan are performed by operating the gradient power supply 4, transmitter 8T, and the receiver 8R, according to the control of the sequencer 5. Echo data which has been received by the RF coil 7, and has been subjected to processing by the receiver 8R, is reconstructed by the calculator 10, whereby image values for each mode are generated.

Thus, control scan and tag scan are performed for the subject and the reference phantom ref1 at the same time for each flow quantification (i.e., for each measurement) for various subjects or the same subject, and data measurement and acquisition are performed for each mode.

Of these, the image measurement value $S_{cont/measured}(\text{ref1})$ is generated from echo signals effected by the control scan (step S22).

Furthermore, the image measurement values $S_{cont/measured}(\text{ref2})$ and the $S_{tag/measured}(\text{ref2})$ are each generated for control scan and tag scan with regard to the reference ref2, which is a ROI positioned on gray matter, from the control image $S_{cont/measured}(x,y)$ and the tag image $S_{tag/measured}(x,y)$ (Steps S23 and S24).

Now, the processing order for the above-described processing shown in Steps S21 through S24 is not restricted to the above-described order, rather, the processing can be performed in whatever order appropriate.

Subsequently, using the data generated or stored in the above-described Steps S21 and S22, the corrected reception gain $G_1$ is computed (Step S25).

$$G_1 = S_{cont/cor}(\text{ref1})/S_{cont/measured}(\text{ref1}) \quad (19)$$

That is, the corrected reception gain $G_1$ is obtained for each measurement.

Note that the differences among individuals is small for the image value $S_{cont/cor}$ with regard to normal gray matter and white matter, an arrangement may be made wherein the corrected reception gain $G_1$ is computed using a known image value $S_{cont/cor}$ for each measurement. Thus, the measurement using the static reference phantom ref1, which has been performed beforehand, can be omitted. Furthermore, in the event that the reception gain $G_1$ itself is a known value, an arrangement may be made wherein a series of measurement and calculation shown in Steps S21 through S22, the known gain value is directly used in processing described below.

Subsequently, description will be made below regarding processing for performing calculation for the scale value (proportional coefficient) $K_{1cor}$ with the corrected reception gain. First of all, ASL image value $\Delta S_{measured}(\text{ref2})$ for the reference ref2 is computed from the generated data in the above-described Steps S23 and S24 with the differential calculation as represented with the following Expression (20) (Step S26).

Mathematical Expression 22

$$\Delta S_{measured}(\text{ref2}) = S_{cont/measured}(\text{ref2}) - S_{tag/measured}(\text{ref2}) \quad (20)$$

Furthermore, using the reception gain $G_1$ corrected in Step S26, the image value $\Delta S_{cor}(\text{ref2})$ for the reference ref2 is computed with the following Expression (21) (Step S27).

$$\Delta S_{cor}(\text{ref2}) = \Delta S_{measured}(\text{ref2}) \times (1/G1) \quad (21)$$

Using the image value $\Delta S_{cor}(\text{ref2})$ thus obtained, the function for polynomial approximation is suitably corrected, and accordingly, flow quantification wherein the influence due to the difference in the reception gain is eliminated can be performed.

With flow quantification described in the various embodiments, flow quantification with higher precision can be performed as compared with the flow quantification with insufficient precision performed with the scaling based upon the conventional single-compartment model.

The present invention has been made based upon the ground obtained from the simulations and experiments which were performed by the present inventor. In particular, the basis is that the two-compartment model is employed as a model representing blood diffusing into tissue, and the values of tracer concentration $Q_t$ for several numbers of values of flow f. Furthermore, a table or a conversion expression is formed for converting the tracer concentration $Q_t$ into the flow f. Moreover, the ASL image:ASL(x,y) obtained with the ASL imaging based upon the ASTAR technique or the like, is normalized into the ASLR image:ASLR(x,y), the tracer flow amount $Q_t(x,y)$ is obtained from the ASLR image, and the tracer flow amount $Q_t(x,y)$ is subjected to a simple scaling processing by using or referring the above-described conversion expression or table, whereby the flow f is quantified for each pixel. Thus, two-dimensional distribution information with regard to the flow f in the head is displayed, for example.

As described above, the two-compartment model is employed as a base model, and not only is the linear scaling based upon linear approximation employed, but also curve approximation using a higher-order polynomial more than a quadric polynomial is employed, and thus flow quantification with higher precision can be performed.

With the quantification, while the two-compartment model is employed without performing measurement for the required parameters for the model, flow quantification can be performed with generally the same precision as with a case of performing measurement for the required parameters. Furthermore, there is no need to measure the parameter T1 for each tissue in the process for quantification, and accordingly, quantification is improved. Moreover, the measured data is signal intensity under a single condition, and processing is performed simply by referring to the table with the tracer concentration $Q_t$ based upon the intensity, thereby enabling the flow f such as blood flow to be quantified in a simple manner.

Note that the above-described curve approximation using a polynomial equation (non-linear scaling) can be applied to scaling based upon the single-compartment model, as well. Conventionally, only the linear scaling based upon the single-compartment model has been known, so improving the precision of the scaling based upon the single-compartment model, which is a simpler model as compared with the two-compartment model, by applying non-linear scaling has great advantages. Also, the scaling based upon the single-compartment model has the advantage of the fact that there is no need to measure the T1 value.

While description has been made with the above-described embodiments regarding a case wherein the imaging portion is the head, imaging can be performed for various portions such as the kidney, the liver, muscle blood flow, and the like.

Note that the present invention is not intended to be restricted to the above-described embodiments given as representative examples; rather, various modifications and changes may be made by one skilled in the art based upon the description of the following claims without departing from the spirit and scope of the present invention, and the present invention encompasses all such modifications and changes.

As described above, with the MRI apparatus, the flow quantification apparatus, and the flow quantification technique, according to the present invention, flow made up of tissue blood flow can be easily quantified from the amount based upon the image data obtained with the ASL imaging, with high precision and with a smaller number of the measurement data sets and smaller amount of calculation, by referring to the corresponding information with regard to the relation between the tracer concentration and the flow stored beforehand, using linear or non-linear scaling.

In particular, the corresponding information (e.g., conversion expression or table) with regard to the relation between the tracer concentration and the flow is formed using the two-compartment model, and stored, so flow quantification can be performed with higher precision using simple calculation. Furthermore, scaling is performed with non-linear approximation using a polynomial, and thus, quantification can be performed for the flow with high precision.

Thus, the flow quantification according to the present invention is particularly effective for a patient affected with acute stage infarction in general, as compared with the conventional techniques wherein a great number of gathered data sets are required and calculation amounts are great, rendering the techniques difficult to use in practice. In the event of displaying the quantified flow as images, comparison having clinical implications can be performed based upon image values, and furthermore, diagnostics wherein the change in flow values is traced for each patient or over time for the same patient, can be provided.

It is needless to say that the present invention is advantageous in that there is no need to administer a constant medium, so imaging can be performed in a noninvasive manner without X-ray exposure.

For the sake of completeness, it should be mentioned that the embodiment explained so far is not a definitive list of possible embodiments of the present invention. The expert will appreciates that it is possible to combine the various construction details or to supplement or modify them by measures known from the prior art without departing from the basic inventive principle.

For example, the quantification technique described above can also be applied to a VS-ASL (Velocity Selective Arterial Spin Labeling) technique. This technique has been known by "Eric C Wong et al., Velocity Selective Arterial Spin Labeling, Proc. Intl. Soc. Mag. Reon. Med. 10 (2002)" and "David G. Norris et al., Velocity Selective Radiofrequency Pulse Trains, Journal of Magnetic Resonance 137, 231-236 (1990)." This application to the VS-ASL technique is very effective when there is a delay in the speed of flow due to a blood capillary packed partly with stenosis, for example, because such a delay is almost compensated by the velocity-selective ASL labeling.

Still, the mode used for the flow quantification according to the present invention is not limited to the two-compartment model, but three or more compartments for, for example, relatively-larger-diameter blood vessels placed adjacently to the foregoing two compartments. This way of placing three or more compartments will lead to flow quantification with more precision.

The entire disclosure of Japanese Patent Application No. 2002-137697 filed on May 13, 2002 including the specification, claims, drawings and summary is incorporated herein by reference in its entirety.

What is claimed is:

1. An MRI (Magnetic Resonance Imaging) apparatus comprising:
    imaging means for acquiring image data by performing an ASL (Arterial Spin Labeling) scan on a patient region to be imaged;
    storing means for storing information indicative of a relationship between a concentration of water tracer and a perfusion flow indicative of blood flow in tissue, the relationship being obtained based on a model that uses two compartments placed respectively inside and outside a flow of blood that diffuses into tissue of the region to be imaged and that takes into account temporal changes in diffusion of blood flow into the tissue; and
    quantifying means for quantifying perfusion in the region to be imaged by using the image data and the relationship information between the tracer concentration and the perfusion flow;
    wherein the quantifying means comprises:
    means configured to obtain a plurality of tracer amounts existing within a unit voxel which respectively correspond to each of a plurality of known flows by applying to the model representative parameters of tissue in the region to be imaged;
    means configured to approximate a relationship between the plurality of known flows and the plurality of tracer amounts using a polynomial expression which directly converts the tracer amounts into known flows using only coefficients of the polynomial expression as parameters; and
    wherein the storing means comprises means configured to store, as correspondence information, a correspondence relationship based on the polynomial expression in the form of either a table or a conversion expression.

2. An MRI (Magnetic Resonance Imaging) apparatus comprising:
    an imaging unit configured to acquire image data by performing an ASL (Arterial Spin Labeling) scan on a region to be imaged;
    a storing unit configured to store information indicative of a relationship between a concentration of water tracer and a perfusion flow indicative of blood flow in tissue, the relationship being obtained based on a model that uses two compartments placed respectively inside and outside a flow of blood that diffuses into tissue of the region to be imaged and that takes into account temporal changes in diffusion of blood flow into the tissue; and
    a flow quantifying unit configured to quantify perfusion flow in the region to be imaged by using the image data and the relationship information between the tracer concentration and the perfusion flow;
    wherein the flow quantifying unit comprises:
    means configured to obtain a plurality of tracer amounts existing within a unit voxel which respectively correspond to each of a plurality of known flows by applying to the model representative parameters of tissue in the region to be imaged;
    means configured to approximate a relationship between the plurality of known flows and the plurality of tracer amounts using a polynomial expression which directly converts the tracer amounts into known flows using only coefficients of the polynomial expression as parameters; and
    wherein the storing unit comprises means configured to store, as correspondence information, a correspondence relationship based on the polynomial expression in the form of either a table or a conversion expression.

3. The MRI apparatus according to claim 2, wherein the flow quantifying unit comprises:
    means configured to obtain an amount of the tracer within a unit voxel from signal intensities of image data based on the ASL scan; and
    means configured to convert the amount of the tracer into the perfusion flow using either the table or the conversion expression.

4. The MRI apparatus according to claim 3, wherein the obtaining means is configured to obtain an ASLR (ASL signal to control signal ratio image) from the image data based on the ASL scan and to calculate the amount of the tracer using the ASLR image.

5. The MRI apparatus according to claim 2, wherein the storing unit comprises means configured to use reference data to correct the correspondence relationship between the tracer concentration and the perfusion flow.

6. A flow quantification apparatus in which a model indicating a diffusion state of a flow of blood that diffuses into tissue of a subject region to be imaged is used for quantifying a perfusion flow in the region to be imaged, the apparatus comprising:
    a magnetic resonance imaging (MRI) means for performing magnetic resonance imaging of a subject region;
    a storing unit configured to store correspondence information between a concentration of water tracer and a perfusion flow indicative of blood flow in tissue of the region to be imaged, the relationship being obtained based on a model that uses two compartments placed respectively inside and outside the flow of blood that diffuses into tissue of the region to be imaged and that takes into account temporal changes in diffusion of blood flow into the tissue; and
    a flow quantifying unit configured to quantify the perfusion flow in the region to be imaged by using image data obtained by imaging means and the correspondence information between the tracer concentration and the perfusion flow;

wherein the flow quantifying unit comprises:
means configured to obtain a plurality of amounts of the tracer existing within a unit voxel which each respectively correspond to one of a plurality of known flows by applying to a model representative parameters of tissue in the region to be imaged;
means configured to approximate a relationship between the plurality of known flows and the plurality of amounts of the tracer using a polynomial expression which directly converts the tracer amounts into known flows using only coefficients of the polynomial expression as parameters; and
wherein the storm unit comprises means configured to store, as the correspondence information, a correspondence relationship based on the polynomial expression in the form of either a table or a conversion expression, the correspondence relationship being applied to quantifying the perfusion flow in the region to be imaged.

7. The flow quantification apparatus according to claim 6, wherein the imaging means is configured to obtain the image data by performing a scan based on a VS-ASL (Velocity Selective Arterial Spin Labeling) technique.

8. A flow quantification method in which a model indicating a diffusion state of a flow of blood that diffuses into tissue of a region to be imaged of a subject to be examined is used for quantifying a perfusion flow in the region to be imaged, said method comprising:
use of a magnetic resonance imaging (MRI) means to acquire MRI data from patient tissue of a region to be imaged, including:
storing correspondence information between a concentration of water tracer and perfusion flow indicative of blood flow in tissue of the region to be imaged, the relationship being obtained based on a model that uses two compartments placed respectively inside and outside the flow of blood that diffuses into tissue of the region to be imaged and that takes into account temporal changes in diffusion of blood flow into the tissue; and
quantifying perfusion flow in the region to be imaged by using image data of the subject and the correspondence information between the tracer concentration and the perfusion flow;
wherein the quantifying step comprises:
obtaining a plurality of amounts of the tracer existing within a unit voxel which each respectively correspond to one of plural known flows by applying, to the model, representative parameters of the tissue in the region to be imaged;
approximating a relationship between the plurality of known flows and the plurality of amounts of the tracer using a polynomial expression which directly converts the tracer amounts into known flows using only coefficients of the polynomial expression as parameters; and
wherein the storing step comprises storing as the correspondence information, a correspondence relationship based on the polynomial expression in the form of either a table or a conversion expression.

* * * * *